(12) United States Patent
Tani et al.

(10) Patent No.: US 7,928,232 B2
(45) Date of Patent: Apr. 19, 2011

(54) METHOD FOR PRODUCING ASYMMETRIC TETRASUBSTITUTED CARBON ATOM-CONTAINING COMPOUND

(75) Inventors: Yuichiro Tani, Edogawa-ku (JP); Yutaka Kitagawa, Edogawa-ku (JP); Makoto Muto, Edogawa-ku (JP); Toshiaki Jyono, Edogawa-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 690 days.

(21) Appl. No.: 11/914,952

(22) PCT Filed: May 19, 2006

(86) PCT No.: PCT/JP2006/309996
§ 371 (c)(1), (2), (4) Date: Dec. 6, 2007

(87) PCT Pub. No.: WO2006/123767
PCT Pub. Date: Nov. 23, 2006

(65) Prior Publication Data
US 2009/0054648 A1 Feb. 26, 2009

(30) Foreign Application Priority Data

May 20, 2005 (JP) ................................. 2005-148121
Jun. 15, 2005 (JP) ................................. 2005-174656

(51) Int. Cl.
*C07F 5/02* (2006.01)
*C07D 211/00* (2006.01)
*C07D 209/54* (2006.01)
*C07C 61/04* (2006.01)

(52) U.S. Cl. ............. 546/13; 546/15; 548/408; 562/506
(58) Field of Classification Search .................... 546/13, 546/15; 562/506; 548/408
See application file for complete search history.

(56) References Cited

U.S. PATENT DOCUMENTS

| 5,547,962 | A * | 8/1996 | Ito et al. ...................... 514/312 |
| 7,563,805 | B2 | 7/2009 | Takahashi et al. |
| 2008/0300403 | A1 * | 12/2008 | Nishimoto .................... 544/101 |

FOREIGN PATENT DOCUMENTS

| JP | 3 95176 | 4/1991 |
| JP | 94 14794 | 7/1994 |
| JP | 7 224033 | 8/1995 |
| JP | 7 285934 | 10/1995 |
| JP | 7 309864 | 11/1995 |
| JP | 9 208561 | 8/1997 |

OTHER PUBLICATIONS

Extended European Search Report issued Sep. 27, 2010, in Application No. 06746652.4-2101 / 1882685 PCT/JP2006309996.
Toshihiko Yoshida, et al., "Studies on Quinolone Antibacterials. V.1) Synthesis and Antibacterial Activity of Chiral 5-Amino-7-(-4-substituted-3-amino-1-pyrrolidinyl)-6-fluoro-1,4-dihydro-8-methyl-4-oxoquinoline-3-carboxylic Acid and Derivatives", Chem. Pharm. Bull., vol. 44, No. 7, (Pharmaceutical Society of Japan, XP002942278, 1996, pp. 1376-1386.

\* cited by examiner

*Primary Examiner* — Nizal S Chandrakumar
(74) *Attorney, Agent, or Firm* — Oblon, Spivak, McClelland, Maier & Neustadt, L.L.P.

(57) ABSTRACT

The invention provides an industrial method for producing a spiroaminopyrrolidone derivative, which is an intermediate for producing a quinolone antibacterial agent.
The invention provides a method for producing a compound represented by formula (2):

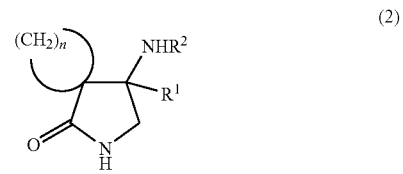

(2)

(wherein n is an integer of 2 to 5; $R^1$ represents a (substituted) alkyl group or a (substituted) aryl group; and $R^2$ represents a (substituted) alkoxycarbonyl group, a (substituted) aralkyloxycarbonyl group, a (substituted) aliphatic acyl group, or a (substituted) aromatic acyl group), which includes treating a compound represented by formula (1):

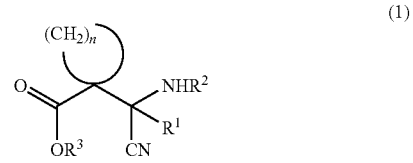

(1)

(wherein n, $R^1$, and $R^2$ are the same as defined above; and $R^3$ represents a hydrogen atom, a (substituted) alkyl group, or a (substituted) aralkyl group) under a hydrogen gas atmosphere in the presence of a metallic catalyst.

5 Claims, 1 Drawing Sheet

METHOD FOR PRODUCING ASYMMETRIC TETRASUBSTITUTED CARBON ATOM-CONTAINING COMPOUND

TECHNICAL FIELD

The present invention relates to a method for producing a quinolone derivative which is expected to serve as an excellent antibacterial agent, to an intermediate compound that is useful in the production method, and to a method for producing the intermediate.

BACKGROUND ART

In respiratory infectious diseases, multi-drug-resistant Pneumococcus is the most serious therapeutic target. Telithromycin, which is considered as the most effective drug against the Pneumococcus, induces a grave side effect; i.e., consciousness disorders. Therefore, development of an antibacterial agent which exhibits high antibacterial effect and induces reduced side effect is envisaged.

Under such circumstances, the present applicant previously found that quinolone compounds represented by formula (I):

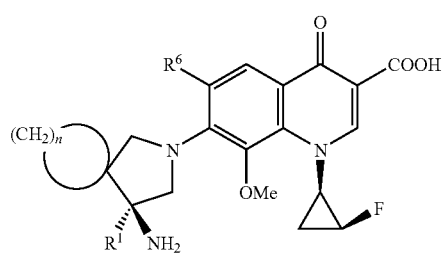

(I)

(wherein n is an integer of 2 to 5; $R^1$ represents a C1 to C4 alkyl group which may have a substituent, or an aryl group which may have a substituent; and $R^6$ represents a hydrogen atom or a fluorine atom) can solve problems in the therapy of respiratory infectious diseases; for example, these compounds exhibit excellent bactericidal effect on multi-drug-resistant Pneumococcus as well as high safety and excellent in vivo behavior, and filed a patent application therefor (Patent Document 1). These compounds can be produced through condensation reaction between a spiroaminopyrrolidine compound having an asymmetric tetrasubstituted carbon atom represented by (6-1):

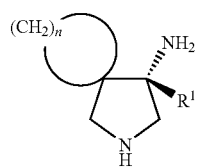

(6-1)

or such a spiroaminopyrrolidine compound in which the amino group attached to the ring is protected by a protective group and a boron-chelate of a quinolone-skeleton compound represented by, for example, the following formula:

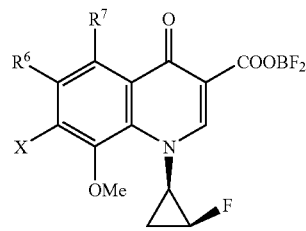

or a carboxylic form of the quinolone-skeleton compound instead of the boron-chelated compound.

Among compounds represented by formula (6-1), a compound in which, for example, $R^1$ is a methyl and n is 2 can be synthesized through the following steps: cyclization reaction between t-butyl acetoacetate (starting material) and alkylene dihalide; converting the formed cyclic compound to an amino-cyano compound by use of a cyanide compound (i.e., Strecker reaction); reducing the cyano group of the amino-cyano compound to convert to an aminomethyl group, thereby forming a diamino compound; performing ring-closure reaction through intramolecular lactamization between the amino group derived from the cyano group of the compound and a carboxylic moiety of the compound, to thereby form a spiroaminopyrrolidone compound having an asymmetric tetrasubstituted carbon atom; subsequently, protecting the amino group and the NH group of the pyrrolidone moiety of the compound; performing optical resolution of the racemic mixture through HPLC by use of an optically active column, to thereby form an optically active form; reducing pyrrolidone; and finally, removing the protective group attached to the ring nitrogen atom. The thus-proposed method isolates a single-isomer intermediate compound which can be employed in introduction of a substituent to the 7-position of a quinolone ring and which is used for producing a single-isomer compound represented by formula (I).

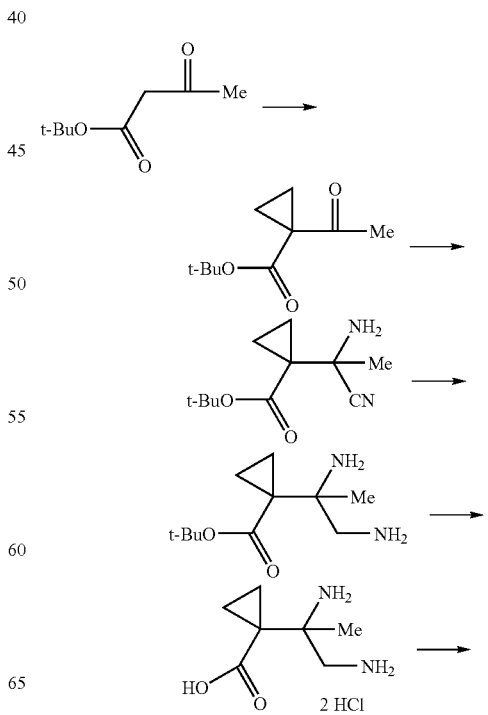

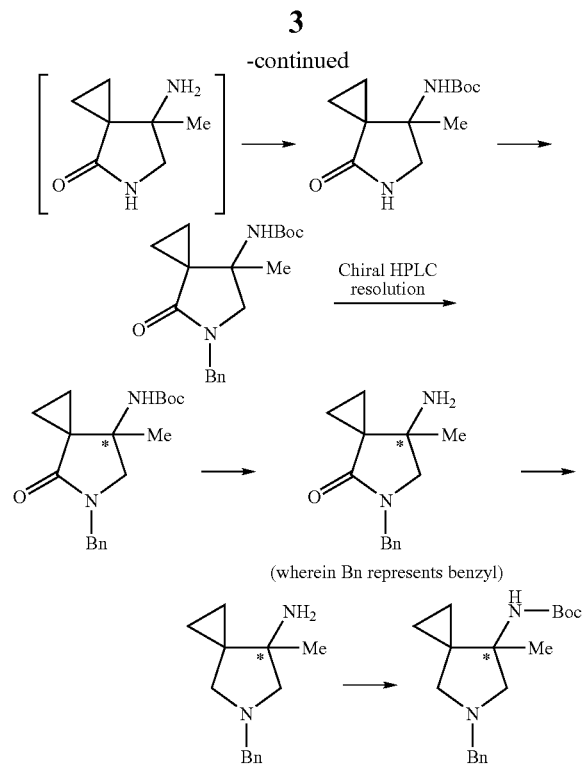

(wherein Bn represents benzyl)

Meanwhile, there has been known a method for producing a spiro-ring-structure pyrrolidine compound having no alkyl group at the 3-position of its pyrrolidine ring (Patent Document 2).

Patent Document 1: JP 2005-146386
Patent Document 2: JP 09-208561

DISCLOSURE OF THE INVENTION

Problems to be Solved by the Invention

A study on industrial-scale application of the proposed production method has revealed that, in a step of the aforementioned steps in which the cyano group of the amino-cyano compound is reduced to produce an intermediate to be ring-closed to form a spiroaminopyrrolidone, retro-reaction of the amino-cyano compound proceeds, to cause elimination of the cyano group, whereby a starting material of Strecker reaction is produced to thereby lower the yield of the target compound, and, as well, highly poisonous cyanide is possibly released. It has also been revealed that, since the diamino compound formed through reduction in the step serves as a poison to a metallic reduction catalyst, such a catalyst must be used in a large amount. Thus, the aforementioned production method has been found to have problems in terms of yield, operability, and environment, for application of the method on an industrial scale. In addition, in the aforementioned production method, there has been proposed a subsequent step for recovering an optically active form through HPCL employing an optically active column. However, this recovery step is cumbersome in an industrial production method and, therefore, requires considerable improvement.

Thus, an object of the present invention is to find a method for obtaining high-purity optically active compound which method avoids problems including release of cyanide generated during carrying out of the aforementioned method on an industrial scale, use of a large amount of catalyst, and performing recovery through HPLC employing an optically active column and which realizes suppression of release of cyanide, reduction in amount of catalyst, and formation of a salt with an optically active acid.

Means for Solving the Problems

The extensive study by the present inventors has revealed that the retro-reaction can be prevented by protecting the amino group of amino-cyano compound produced through Strecker reaction with an electron-attractive group, whereby release of cyanide during reduction can be prevented (i.e., formation of a poisonous substance can be prevented), and the production yield can be elevated. In addition, since the amino group is protected, catalyst inhibiting effect is suppressed (i.e., problematic catalyst poisoning can be prevented).

The present inventors have conducted a further study in an attempt to develop a more efficient production method, and have found that, when an ethyl ester is used as a starting material instead of a t-butyl ester, reaction steps from reduction of the cyano group to cyclization through intramolecular lactamization proceed all at once.

The inventors have also found that a compound in which the cyclic amide moiety has been reduced can be optically resolved through formation of a salt with an optically active acid. Thus, a method for synthesizing an optically active spiroaminopyrrolidine compound having asymmetric tetrasubstituted carbon has been accomplished.

The inventors have also developed an effective method of condensing the optically active compound and a quinolone derivative, thereby realizing an industrially advantageous method for producing a synthetic antibacterial agent. In other words, the inventors have found that the target compound can be produced efficiently without introducing a protective group to the spiroaminopyrrolidine derivative. Thus, the inventors achieved reduction of the number of reaction steps as well as improvement of production yield.

Accordingly, the present invention provides the following.
[1] A method for producing a compound represented by formula (2):

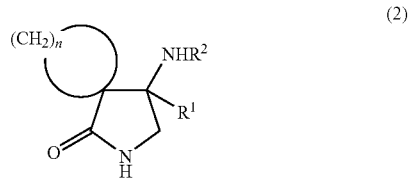

(2)

(wherein n is an integer of 2 to 5; $R^1$ represents a C1 to C4 alkyl group which may have a substituent or an aryl group which may have a substituent; and $R^2$ represents an alkoxycarbonyl group which may have a substituent, an aralkyloxycarbonyl group which may have a substituent, an aliphatic acyl group which may have a substituent, or an aromatic acyl group which may have a substituent), which comprises treating a compound represented by formula (1):

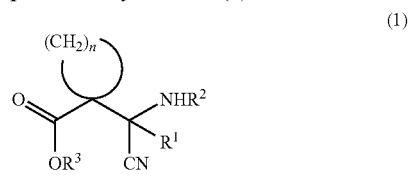

(1)

(wherein n, $R^1$, and $R^2$ are the same as defined above; and $R^3$ represents a C1 to C4 alkyl group which may have a substituent, an aralkyl group which may have a substituent, or a hydrogen atom) under a hydrogen gas atmosphere in the presence of a metallic catalyst.

[2] A compound represented by formula (1):

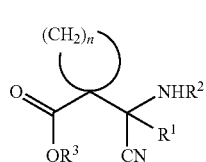
(1)

(wherein n is an integer of 2 to 5; $R^1$ represents a C1 to C4 alkyl group which may have a substituent or an aryl group which may have a substituent; $R^2$ represents an alkoxycarbonyl group which may have a substituent, an aralkyloxycarbonyl group which may have a substituent, an aliphatic acyl group which may have a substituent, or an aromatic acyl group which may have a substituent; and $R^3$ represents a C1 to C4 alkyl group which may have a substituent, an aralkyl group which may have a substituent, or a hydrogen atom).

[3] A compound represented by formula (2):

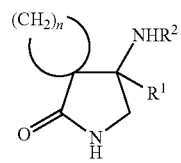
(2)

(wherein n is an integer of 2 to 5; $R^1$ represents a C1 to C4 alkyl group which may have a substituent or an aryl group which may have a substituent; and $R^2$ represents an alkoxycarbonyl group which may have a substituent, an aralkyloxycarbonyl group which may have a substituent, an aliphatic acyl group which may have a substituent, or an aromatic acyl group which may have a substituent).

[4] A compound represented by formula (3):

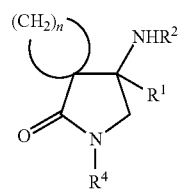
(3)

(wherein n is an integer of 2 to 5; $R^1$ represents a C1 to C4 alkyl group which may have a substituent or an aryl group which may have a substituent; $R^2$ represents an alkoxycarbonyl group which may have a substituent, an aralkyloxycarbonyl group which may have a substituent, an aliphatic acyl group which may have a substituent, or an aromatic acyl group which may have a substituent; and $R^4$ represents a benzyl group, a benzhydryl group, or a trityl group, wherein phenyl group thereof may have, as a substituent, one or more groups selected from the group consisting of a nitro group, an alkoxy group, and a halogen atom).

[5] A compound represented by formula (4):

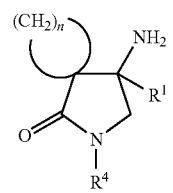
(4)

(wherein n is an integer of 2 to 5; $R^1$ represents a C1 to C4 alkyl group which may have a substituent or an aryl group which may have a substituent; and $R^4$ represents a benzyl group, a benzhydryl group, or a trityl group, wherein phenyl group thereof may have, as a substituent, one or more groups selected from the group consisting of a nitro group, an alkoxy group, and a halogen atom).

[6] A method for producing a salt formed from an optically active carboxylic acid and a compound represented by formula (5-1):

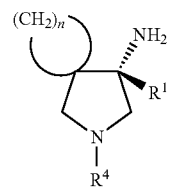
(5-1)

or formula (5-2):

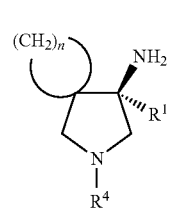
(5-2)

(wherein n is an integer of 2 to 5; $R^1$ represents a C1 to C4 alkyl group which may have a substituent or an aryl group which may have a substituent; and $R^4$ represents a benzyl group, a benzhydryl group, or a trityl group, wherein phenyl group thereof may have, as a substituent, one or more groups selected from the group consisting of a nitro group, an alkoxy group, and a halogen atom) or a hydrate thereof, which comprises treating a compound represented by formula (5):

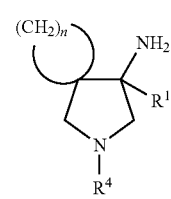
(5)

(wherein n, $R^1$, and $R^4$ are the same as defined above) with an optically active carboxylic acid in an organic solvent.

[7] A salt formed from an optically active carboxylic acid and a compound represented by formula (5-1):

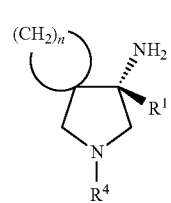
(5-1)

(wherein n is an integer of 2 to 5; $R^1$ represents a C1 to C4 alkyl group which may have a substituent or an aryl group which may have a substituent; and $R^4$ represents a benzyl group, a benzhydryl group, or a trityl group, wherein phenyl group thereof may have, as a substituent, one or more groups selected from the group consisting of a nitro group, an alkoxy group, and a halogen atom) or a hydrate thereof.

[8] A salt formed from an optically active carboxylic acid and a compound represented by (5-2):

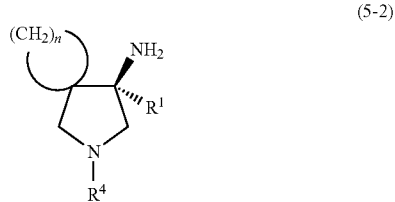
(5-2)

(wherein n is an integer of 2 to 5; $R^1$ represents a C1 to C4 alkyl group which may have a substituent or an aryl group which may have a substituent; and $R^4$ represents a benzyl group, a benzhydryl group, or a trityl group, wherein phenyl group thereof may have, as a substituent, one or more groups selected from the group consisting of a nitro group, an alkoxy group, and a halogen atom) or a hydrate thereof.

[9] A compound represented by the following formula:

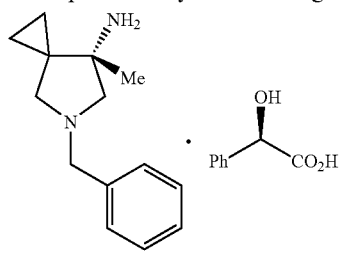

or a hydrate thereof.

[10] A compound represented by the following formula:

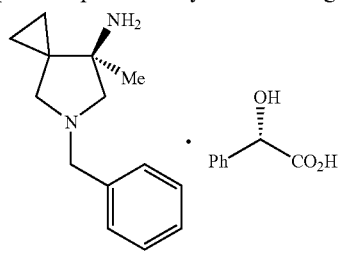

or a hydrate thereof.

[11] A method for producing a compound represented by formula (5-1):

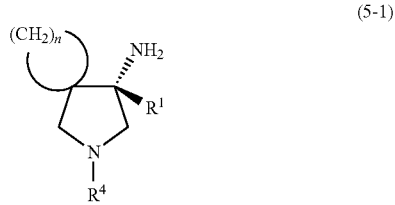
(5-1)

(wherein n is an integer of 2 to 5; $R^1$ represents a C1 to C4 alkyl group which may have a substituent or an aryl group which may have a substituent; and $R^4$ represents a benzyl group, a benzhydryl group, or a trityl group, wherein phenyl group thereof may have, as a substituent, one or more groups selected from the group consisting of a nitro group, an alkoxy group, and a halogen atom), which comprises treating a salt formed from an optically active carboxylic acid and a compound represented by formula (5-1):

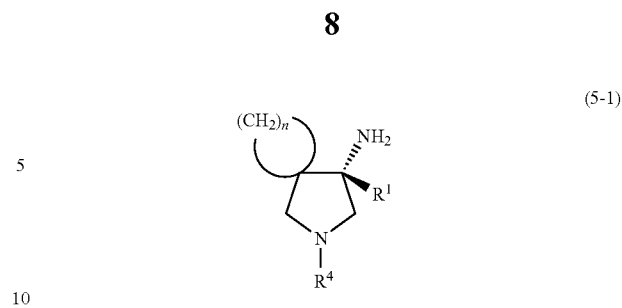
(5-1)

(wherein n, $R^1$, and $R^4$ are the same as defined above) with a base.

[12] A method for producing a compound represented by formula (5-2):

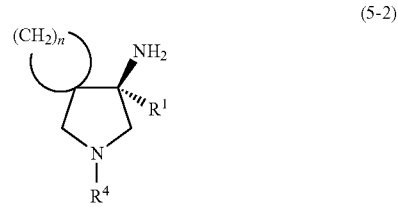
(5-2)

(wherein n is an integer of 2 to 5; $R^1$ represents a C1 to C4 alkyl group which may have a substituent or an aryl group which may have a substituent; and $R^4$ represents a benzyl group, a benzhydryl group, or a trityl group, wherein phenyl group thereof may have, as a substituent, one or more groups selected from the group consisting of a nitro group, an alkoxy group, and a halogen atom), characterized in that the method comprises treating a salt formed from an optically active carboxylic acid and a compound represented by formula (5-2):

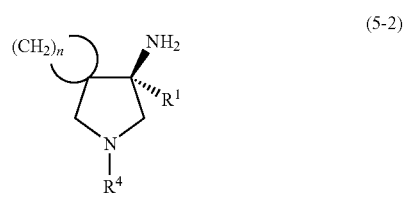
(5-2)

(wherein n, $R^1$, and $R^4$ have the same meanings as defined above) with a base.

[13] A compound represented by formula (5-1):

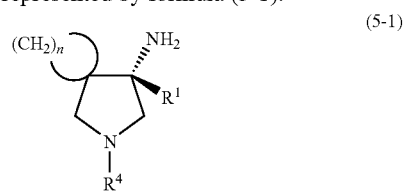
(5-1)

(wherein n is an integer of 2 to 5; $R^1$ represents a C1 to C4 alkyl group which may have a substituent or an aryl group which may have a substituent; and $R^4$ represents a benzyl group, a benzhydryl group, or a trityl group, wherein phenyl group thereof may have, as a substituent, one or more groups selected from the group consisting of a nitro group, an alkoxy group, and a halogen atom), a salt of the compound, or a hydrate of any of these.

[14] A compound represented by formula (5-2):

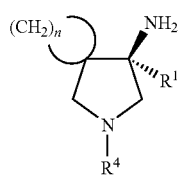

(5-2)

(wherein n is an integer of 2 to 5; $R^1$ represents a C1 to C4 alkyl group which may have a substituent or an aryl group which may have a substituent; and $R^4$ represents a benzyl group, a benzhydryl group, or a trityl group, wherein phenyl group thereof may have, as a substituent, one or more groups selected from the group consisting of a nitro group, an alkoxy group, and a halogen atom), a salt of the compound, or a hydrate of any of these.

[15] A compound represented by the following formula.

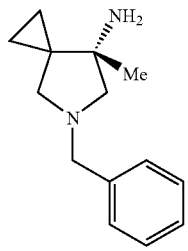

[16] A compound represented by the following formula.

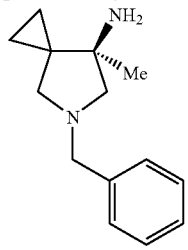

[17] A method for producing a compound represented by formula (6):

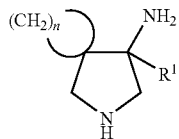

(6)

(wherein n is an integer of 2 to 5; and $R^1$ represents a C1 to C4 alkyl group which may have a substituent or an aryl group which may have a substituent) or an optically active form thereof, which comprises treating a compound represented by formula (51):

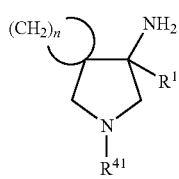

(51)

(wherein n and $R^1$ are the same as defined above; $R^{41}$ represents a benzyl group or a benzhydryl group, wherein phenyl group thereof may have, as a substituent, one or more groups selected from the group consisting of a nitro group, an alkoxy group, and a halogen atom) or an optically active form thereof in an acidic solvent in the presence of a metallic catalyst, and under a hydrogen gas atmosphere or in the presence of formic acid.

[18] A compound represented by formula (7):

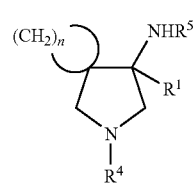

(7)

(wherein n is an integer of 2 to 5; $R^1$ represents a C1 to C4 alkyl group which may have a substituent or an aryl group which may have a substituent; $R^4$ represents a benzyl group, a benzhydryl group, or a trityl group, wherein phenyl group thereof may have, as a substituent, one or more groups selected from the group consisting of a nitro group, an alkoxy group, and a halogen atom; and $R^5$ represents a t-butyloxycarbonyl group, a benzyloxycarbonyl group, a benzoyl group, or an acetyl group), an optically active form of the compound, a salt of any of these, or a hydrate of any of these.

[19] A compound represented by formula (6):

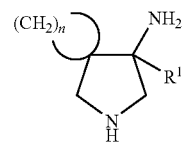

(6)

(wherein n is an integer of 2 to 5; and $R^1$ represents a C1 to C4 alkyl group which may have a substituent or an aryl group which may have a substituent), an optically active form of the compound, a salt of any of these, or a hydrate of any of these.

[20] A compound represented by the following formula, an optically active form of the compound, or a hydrate of any of these.

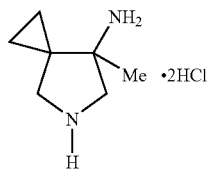

[21] A compound represented by formula (8):

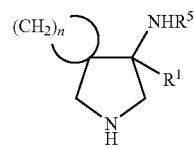

(8)

(wherein n is an integer of 2 to 5; $R^1$ represents a C1 to C4 alkyl group which may have a substituent or an aryl group which may have a substituent; and $R^5$ represents a t-butyloxycarbonyl group, a benzyloxycarbonyl group, a benzoyl group, or an acetyl group), an optically active form of the compound, a salt of these, or a hydrate of any of these.

[22] A method for producing a compound represented by formula (9-1):

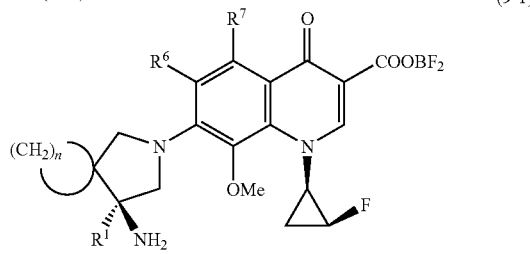

(9-1)

(wherein n is an integer of 2 to 5; $R^1$ represents a C1 to C4 alkyl group which may have a substituent or an aryl group which may have a substituent; $R^6$ represents a hydrogen atom or a fluorine atom; and $R^7$ represents an amino group which may have a substituent, a C1 to C4 alkoxy group which may have a substituent, a hydrogen atom, or a hydroxyl group), which comprises reacting a compound represented by formula (6-1):

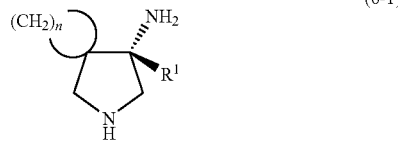

(6-1)

(wherein n and $R^1$ are the same as defined above) or a salt thereof with a boron-chelate of a quinolon-skeleton compound represented by the following formula:

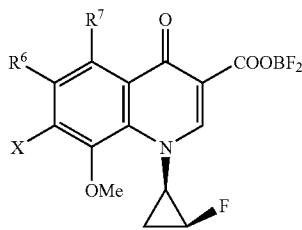

(wherein $R^6$ and $R^7$ are the same as defined above; and X represents a leaving group) in the presence of a base.

[23] A method for producing a compound represented by formula (9-2):

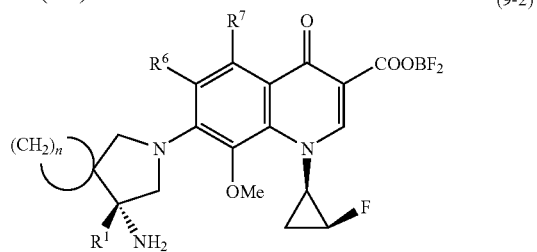

(9-2)

(wherein n is an integer of 2 to 5; $R^1$ represents a C1 to C4 alkyl group which may have a substituent or an aryl group which may have a substituent; $R^6$ represents a hydrogen atom or a fluorine atom; and $R^7$ represents an amino group which may have a substituent, a C1 to C4 alkoxy group which may have a substituent, a hydrogen atom, or a hydroxyl group), which comprises reacting a compound represented by formula (6-2):

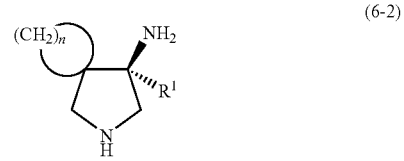

(6-2)

(wherein n and $R^1$ are the same as defined above) or a salt thereof with a boron-chelate of a quinolon-skeleton compound represented by the following formula:

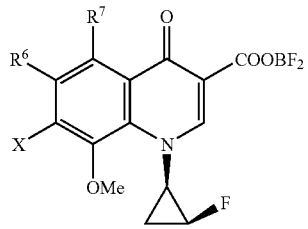

(wherein $R^6$ and $R^7$ are the same as defined above; and X represents a leaving group) in the presence of a base.

[24] A compound represented by formula (9-1):

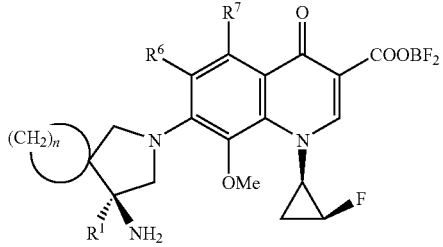

(9-1)

(wherein n is an integer of 2 to 5; $R^1$ represents a C1 to C4 alkyl group which may have a substituent or an aryl group which may have a substituent; $R^6$ represents a hydrogen atom or a fluorine atom; and $R^7$ represents an amino group which may have a substituent, a C1 to C4 alkoxy group, a hydrogen atom, or a hydroxyl group), a salt of the compound, or a hydrate of any of these.

[25] A compound represented by formula (9-2):

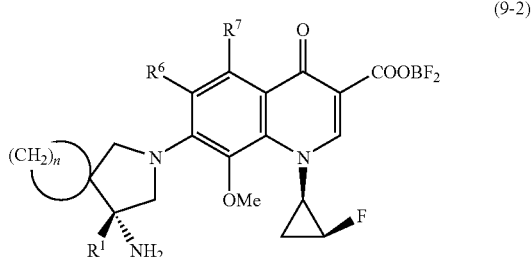

(9-2)

(wherein n is an integer of 2 to 5; $R^1$ represents a C1 to C4 alkyl group which may have a substituent or an aryl group which may have a substituent; $R^6$ represents a hydrogen atom or a fluorine atom; and $R^7$ represents an amino group which may have a substituent, a C1 to C4 alkoxy group, a hydrogen atom, or a hydroxyl group), a salt of the compound, or a hydrate of any of these.

Effects of the Invention

According to the present invention, the followings are achieved: improvement of product yield by protecting the amino group of an intermediate with an electron-withdrawing group; suppression of production of a poisonous substance; considerable reduction of the amount of catalyst; reduction of the number of steps and improvement of production yield through appropriate choice of an ester; and efficient isolation of an optically active form of a compound for introducing a substituent by achieving optical resolution using an optically active acid. Also, the reaction for producing a target compound rapidly proceeds even though an intermediate have no additional protective group. According to the present invention, a target compound can be produced at high yield in a simple process.

BEST MODES FOR CARRYING OUT THE INVENTION

Figure 1:
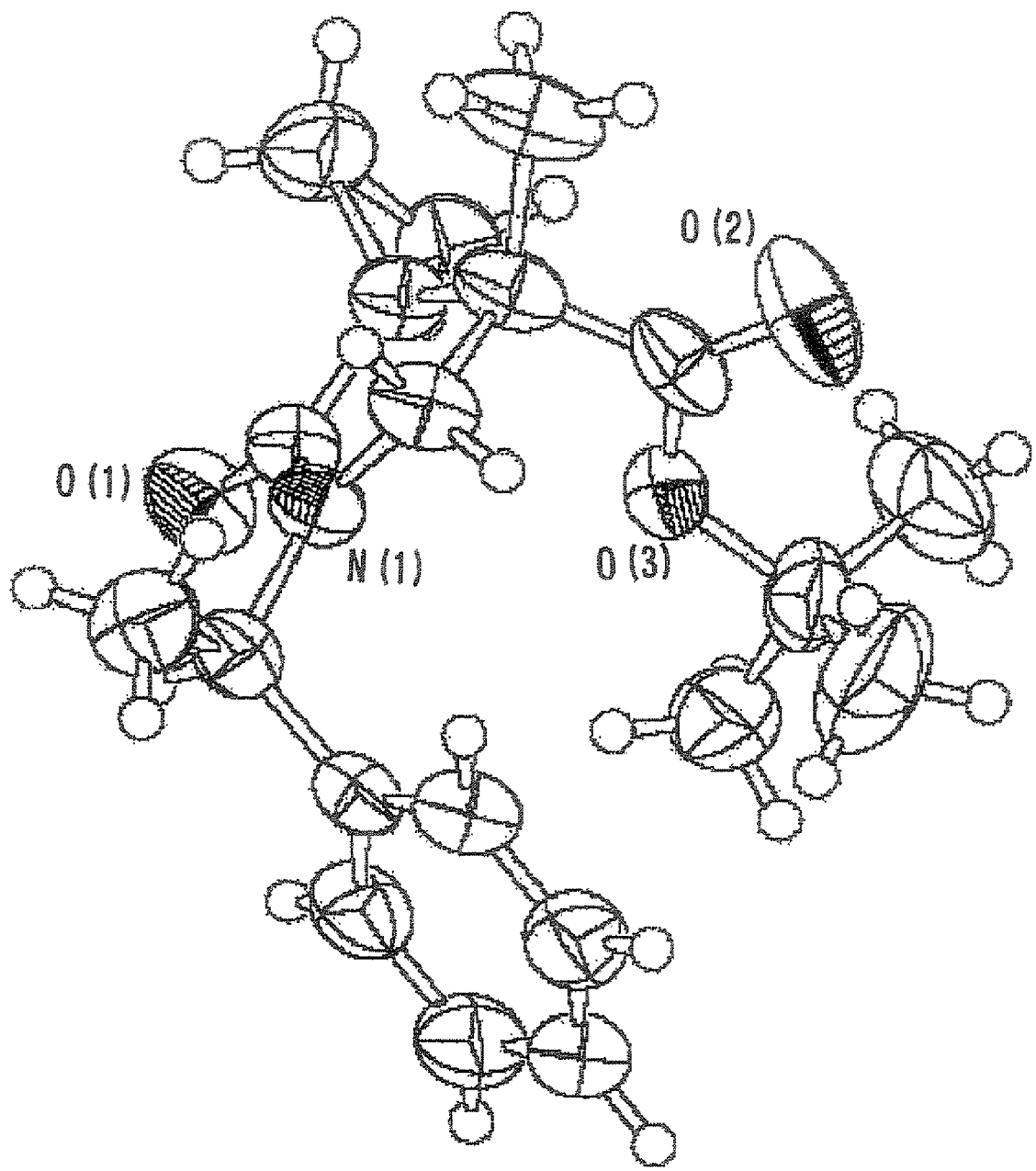
FIG. 1 Results of X-ray structural analysis of the compound produced in Referential Example 6.

The present invention will hereinafter be described in detail.

The compounds of the invention may be produced through, for example, the following scheme.

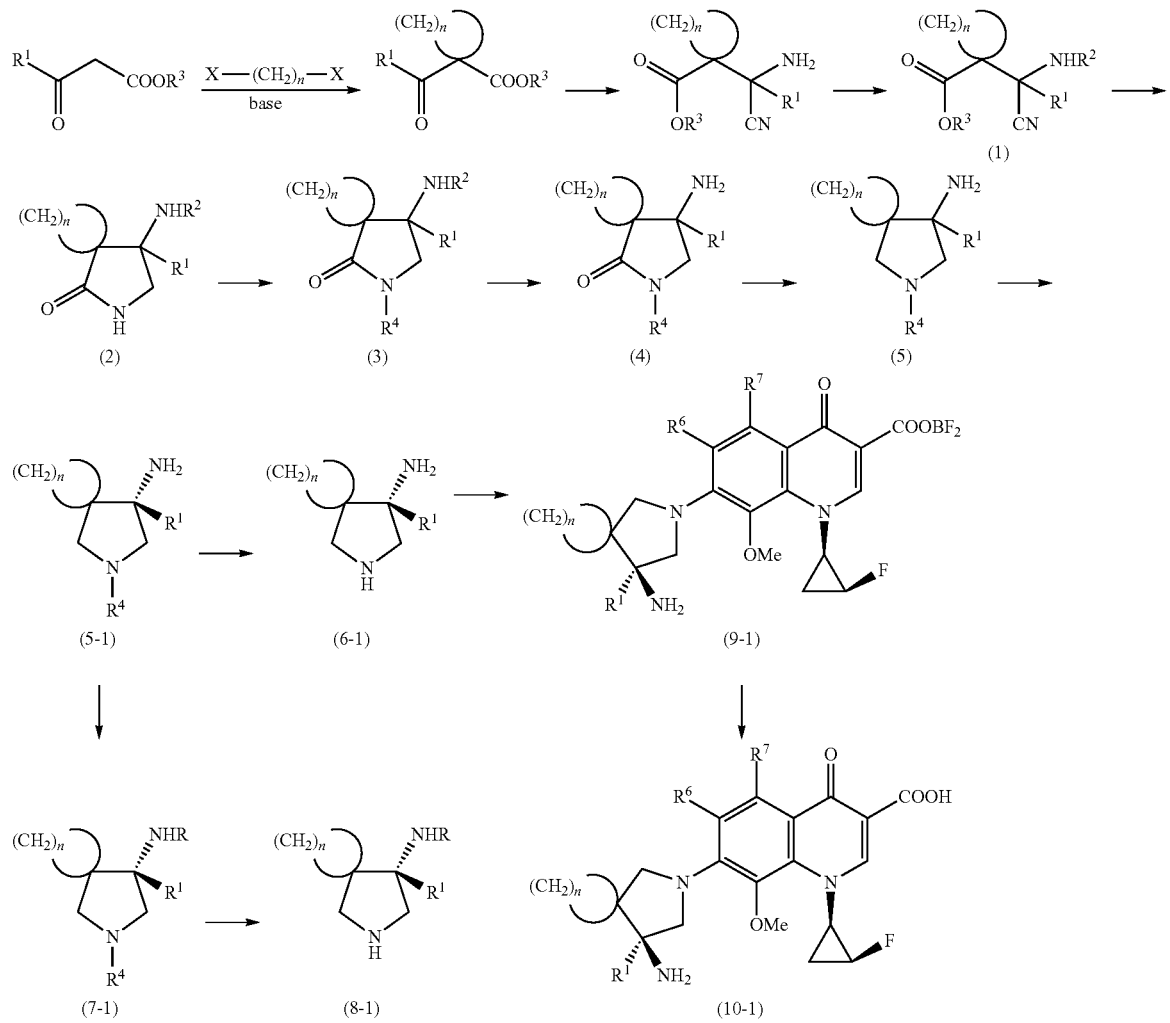

Firstly, a compound represented by formula (1):

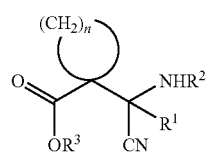

(wherein n is an integer of 2 to 5; $R^1$ represents a C1 to C4 alkyl group which may have a substituent or an aryl group which may have a substituent; $R^2$ represents an alkoxycarbonyl group which may have a substituent, an aralkyloxycarbonyl group which may have a substituent, an aliphatic acyl group which may have a substituent, or an aromatic acyl group which may have a substituent; and $R^3$ represents a C1 to C4 alkyl group which may have a substituent, an aralkyl group which may have a substituent, or a hydrogen atom) (hereinafter a compound may be denoted along with the number of the formula thereof, for example, the above compound is denoted by "compound (1)") can be readily synthesized through the following procedure: reacting a β-keto ester with a 1,2-dihalogenoethane (e.g., dibromoethane or dichloroethane) (for producing a compound in which n is 2, but a dihalgenoalkylene compound having carbon atoms of the number corresponding to n may be generally employed) under basic conditions, to thereby form a cyclic keto ester compound; subjecting the keto ester compound to Strecker reaction with, for example, ammonia, a cyanating agent, and an ammonium salt, to thereby form an amino-cyano compound; and protecting the formed amino group of the amino-cyano compound. These three steps in the production may be performed according to a known method.

The β-keto ester employed in the synthesis of a cyclic keto ester compound is preferably a lower ester of acetoacetic acid; e.g., methyl acetoacetate or ethyl acetoacetate. No particular limitation is imposed on the base employed in reaction of a dihalogenoalkylene compound, and any base may be employed so long as the base can be generally used for alkylation of β-keto ester. Examples include sodium carbonate, potassium carbonate, and sodium hydroxide. No particular limitation is imposed on the solvent, and any solvent may be used so long as it does not inhibit reaction.

The amino-cyano compound may be produced through reaction of a cyclic keto ester compound with ammonia and a cyanating agent. Examples of the cyanating agent include cyanides such as sodium cyanide, potassium cyanide, and tetrabutylammonium cyanide. In the reaction, addition of an ammonium salt such as ammonium chloride or ammonium acetate remarkably accelerates the reaction. No particular limitation is imposed on the solvent, and any solvent may be used so long as it does not inhibit reaction.

When a protective group is introduced to the amino-cyano compound, an amino-protecting agent and the amino-cyano compound may be reacted in the absence of a solvent or in a solvent which does not inhibit the reaction. The protecting agent may be selected in accordance with a protective group to be introduced. Examples of the protecting agent include di-t-butyl dicarbonate, benzyl chloroformate, benzoyl chloride, acetic anhydride, and acetyl chloride.

In the compound represented by formula (1), n is an integer of 2 to 5. Preferably, n is 2.

$R^1$ represents a C1 to C4 alkyl group which may have a substituent or an aryl group which may have a substituent. When $R^1$ is an alkyl group, it may be linear or branched. The alkyl group is preferably methyl, ethyl, propyl, or isopropyl. Of these, methyl and ethyl are preferred, with methyl being more preferred.

The alkyl group may have one or more substituents selected from the group consisting of an amino group, a hydroxyl group, a halogen atom, a C1 to C6 alkylthio group, and a C1 to C6 alkoxy group. The amino group or hydroxyl group is preferably bound to an end carbon atom. For example, aminomethyl, 2-aminoethyl, 2-aminopropyl, 3-aminopropyl, hydroxymethyl, 2-hydroxyethyl, 2-hydroxypropyl, and 3-hydroxypropyl are preferred. When the substituent is a halogen atom, a fluorine atom is preferred. The substitution degree of fluorine atoms in the substituted group may be monofluoro to perfluoro. Examples include monofluoromethyl, difluoromethyl, trifluoromethyl, and 2,2,2-trifluoroethyl. When the substituent is an alkylthio group or an alkoxy group, the substituted group is preferably alkylthiomethyl, alkylthioethyl, alkylthiopropyl, alkoxymethyl, alkoxyethyl, or alkoxypropyl, more preferably methylthiomethyl, ethylthiomethyl, methylthioethyl, methoxymethyl, ethoxymethyl, or methoxyethyl.

When $R^1$ is an aryl group, it may be phenyl, tolyl, or naphthyl, with phenyl being preferred. The aryl groups may have one or more substituents such as a nitro group, an alkoxy group, an alkyl group, and a halogen atom.

$R^2$ represents an alkoxycarbonyl group which may have a substituent, an aralkyloxycarbonyl group which may have a substituent, an aliphatic acyl group which may have a substituent, or an aromatic acyl group which may have a substituent. No particular limitation is imposed on $R^2$, and any group may be employed so long as it is known as a protective group for an amino group. More preferably, $R^2$ is an electron-withdrawing protective group.

No particular limitation is imposed on the alkoxycarbonyl group which may have a substituent, and any such groups may be employed so long as the alkoxy moiety has 1 to 6 carbon atoms. Examples of the substituent include a halogen atom. Examples of the thus-substituted group include t-butyloxycarbonyl and 2,2,2-trichloroethoxycarbonyl.

The aralkyloxycarbonyl group which may have a substituent is preferably an aralkyl group having a phenyl group, and the alkyl moiety is preferably methyl. Thus, the aralkyl group is preferably a benzyl group. Examples of the substituent of the aryl moiety in the aralkyl group include an alkyl group, an alkoxy group, a nitro group, and a halogen atom, with methyl, methoxy, chlorine, and nitro being preferred. Examples of the substituent of the alkyl moiety include an alkyl group, with methyl being preferred. Examples of preferred alkoxycarbonyl groups which may have a substituent include benzyloxycarbonyl, p-methoxybenzyloxycarbonyl, and p-nitrobenzyloxycarbonyl.

No particular limitation is imposed on the aliphatic acyl group which may have a substituent, and any such groups may be employed so long as the number of carbon atoms is 2 to 7. The acyl group may be linear or branched. Examples of the substituent include a halogen atom and an alkoxy group, with chlorine, fluorine, and methoxy being preferred. Examples of preferred aliphatic acyl groups which may have a substituent include acetyl, methoxyacetyl, trifluoroacetyl, chloroacetyl, and pivaloyl.

The aromatic acyl group which may have a substituent is preferably an acyl group having a phenyl group. Examples of the substituent include an alkyl group, an alkoxy group, a nitro group, and a halogen atom, with methyl, methoxy, chlorine, and nitro being preferred. Specifically, the aromatic acyl group which may have a substituent is preferably a benzoyl group, a p-nitrobenzoyl group, or a similar group.

Examples of more preferred groups of $R^2$ include t-butyloxycarbonyl, benzyloxycarbonyl, benzoyl, and acetyl.

$R^3$ represents a C1 to C4 alkyl group which may have a substituent, an aralkyl group which may have a substituent, or a hydrogen atom. The C1 to C4 alkyl group which may have a substituent may be the same as described in relation to $R^1$. The aralkyl group which may have a substituent is preferably an aralkyl group having a phenyl group, and the alkyl moiety is preferably a methyl group. Thus, the aralkyl group is preferably a benzyl group. Examples of the substituent of the aryl moiety in the aralkyl group include an alkyl group, an alkoxy group, a nitro group, and a halogen atom, with methyl, methoxy, chlorine, and nitro being preferred. Examples of the substituent of the alkyl moiety include an alkyl group, with methyl being preferred. Specifically, the aralkyl group which may have a substituent is preferably benzyl, p-methoxybenzyl, p-nitrobenzyl, or a similar group. The aralkyl group may also a α-methylphenethyl equivalent in which the methyl moiety is further substituted by a methyl group.

R³ is preferably a liner short-chain alkyl group, preferably, methyl, ethyl, or propyl, more preferably methyl or ethyl. When R³ is such an alkyl group, an aminomethyl group is formed through reduction of the cyano group, concomitant with ring-closure to pyrrolidone.

Compound (2) represented by formula (2):

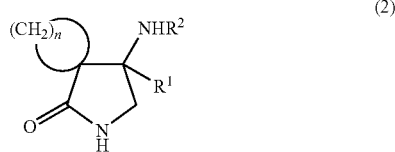

(2)

(wherein n is an integer of 2 to 5; R¹ represents a C1 to C4 alkyl group which may have a substituent or an aryl group which may have a substituent; and R² represents an alkoxycarbonyl group which may have a substituent, an aralkyloxycarbonyl group which may have a substituent, an aliphatic acyl group which may have a substituent, or an aromatic acyl group which may have a substituent) may be produced by treating compound (1) in hydrogen gas under atmospheric pressure or pressurized (≦50 atm) conditions in the presence of a metallic catalyst.

In this reaction, firstly, the cyano group is reduced to form an aminomethyl group, and cyclization concomitantly occurs. Examples of the metallic catalyst employed in the step include Raney nickel, Raney cobalt, palladium carbon, platinum carbon, and rhodium carbon. Of these, Raney nickel, Raney cobalt, and rhodium carbon are preferred.

The reaction temperature may be −30 to 170° C., and is preferably 0 to 110° C.

The reaction is preferably performed in a solvent. Any solvent may be used so long as it does not inhibit the reaction. Preferably, an alcoholic solvent such as methanol or ethanol is employed.

Compound (3) represented by formula (3):

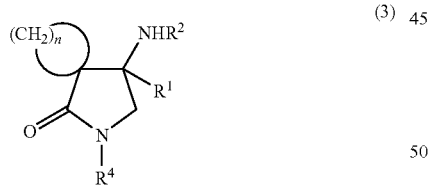

(3)

(wherein n is an integer of 2 to 5; R¹ represents a C1 to C4 alkyl group which may have a substituent or an aryl group which may have a substituent; R² represents an alkoxycarbonyl group which may have a substituent, an aralkyloxycarbonyl group which may have a substituent, an aliphatic acyl group which may have a substituent, or an aromatic acyl group which may have a substituent; and R⁴ represents a benzyl group, a benzhydryl group, or a trityl group, wherein phenyl group thereof may have, as a substituent, one or more groups selected from the group consisting of a nitro group, an alkoxy group, and a halogen atom) may be produced by R⁴-introduction to the nitrogen atom in the lactam ring by reacting compound (2) under basic conditions with an R⁴-forming agent.

Examples of such R⁴-forming agents include benzyl halides such as benzyl chloride and benzyl bromide; benzhydryl halides; and trityl halides.

Examples of the base employed in the step include metal alkoxide and sodium hydride.

Any solvent may be used so long as it does not inhibit the reaction. Preferably, an aprotic polar solvent such as dimethylformamide is employed. The reaction temperature may be −30 to 170° C., and is preferably 0 to 110° C.

In compound (3), R⁴ represents a benzyl group, a benzhydryl group, or a trityl group. The alkyl group and phenyl group thereof may have one or more substituents selected from the group consisting of a nitro group, an alkoxy group, and a halogen atom. R⁴ is preferably a benzyl which may have substituent or a benzhydryl group which may have a substituent, with benzyl, α-methylbenzyl, and benzhydryl being particularly preferred.

Compound (4) represented by formula (4):

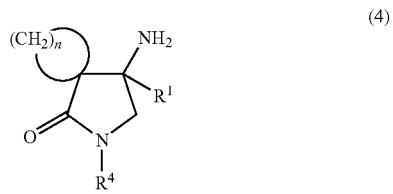

(4)

(wherein n is an integer of 2 to 5; R¹ represents a C1 to C4 alkyl group which may have a substituent or an aryl group which may have a substituent; and R⁴ represents a benzyl group, a benzhydryl group, or a trityl group, wherein phenyl group thereof may have, as a substituent, one or more groups selected from the group consisting of a nitro group, an alkoxy group, and a halogen atom) may be produced by removing the protective group of the amino group of the compound (3). Removal of the protective group may be performed under known conditions depending on the type of the protective group introduced to the amino group.

Compound (5) represented by formula (5):

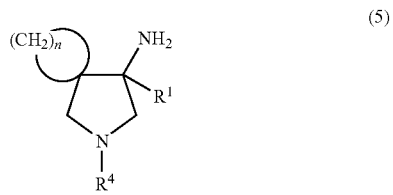

(5)

(wherein n is an integer of 2 to 5; R¹ represents a C1 to C4 alkyl group which may have a substituent or an aryl group which may have a substituent; and R⁴ represents a benzyl group, a benzhydryl group, or a trityl group, wherein phenyl group thereof may have, as a substituent, one or more groups selected from the group consisting of a nitro group, an alkoxy group, and a halogen atom) may be produced by reducing the carbonyl group in the amide moiety present as cyclic pyrrolidone in the compound (4).

Examples of the reducing agent employed in the reduction of the carbonyl group include aluminum hydride agents such as lithium aluminum hydride and sodium bis(2-methoxyethoxy)aluminum hydride and boron hydride agents such as sodium boron hydride, diborane, and borane-tetrahydrofuran complex. Any reaction solvent may be employed so long as it does not inhibit the reaction, and ether compounds such as tetrahydrofuran, diethyl ether, dioxane, and dimethoxyethane; and aromatic compounds such as benzene, toluene, and xylene are preferred. The reaction temperature may be −30 to 170° C., and is preferably 0 to 110° C.

Since $R^2$ present in compound (3) is a protective group containing a carbonyl group, this must be removed in consideration of the characteristics of the reducing agent used for conversion to compound (5).

Therefore, if $R^2$ does not change in the reduction step, this removal may be omitted.

The carbon atom in compound (5) to which a ring amino group has been bound is an asymmetric carbon atom. Therefore, compound (5) includes two antipodal isomers, which are represented by formulas (5-1) and (5-2).

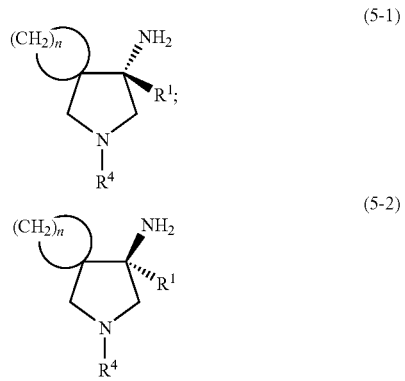

The compound represented by formula (5-1) or (5-2) may be produced by treating compound (5) (racemic mixture) with an optically active carboxylic acid or an optically active sulfonic acid in an organic solvent, to thereby form crystals of an amine salt of the optically active acid. Thus, each optically active form can be isolated through racemic resolution. Examples of the optically active acid employable in racemic resolution include carboxylic acids such as mandelic acid, malic acid, lactic acid, and tartaric acid; and sulfonic acids such as camphorsulfonic acid. Of these, mandelic acid is particularly preferred.

The amount of mandelic acid employed in racemic resolution may be 1 to 1.2 equivalents with respect to the optical isomer which is contained in the racemic mixture and is to be isolated. Examples of the solvent employed in the racemic resolution include aromatic compounds such as benzene, toluene, and xylene; ether compounds such as tetrahydrofuran, diethyl ether, dioxane, and dimethoxyethane; haloaliphatic hydrocarbon solvents such as methylene chloride and chloroform; aliphatic hydrocarbon solvents such as hexane and heptane; and ketonic solvents such as acetone and methyl ethyl ketone. Of these, aromatic compounds such as benzene, toluene, and xylene are preferred, with toluene being particularly preferred. Crystallization temperature is −40° C. to 30° C., preferably −20° C. to 0° C. Notably, these conditions may be applied not only to mandelic acid but also to other optically active acids.

After a target antipode has been isolated as an optically active acid salt, an amine salt of the opposite stereoisomer of compound (5) can be produced by treating the filtrate with a base such as aqueous sodium hydroxide to thereby remove the optically active acid and adding an optically active acid having an opposite stereoproperty to the solution for crystallization. Furthermore, by treating the filtrate obtained in the second crystallization with aqueous sodium hydroxide or the like to thereby remove carboxylic acid and adding the first optically active acid, an amine salt of the optically active acid can further be isolated.

Mandelic acid is a suitable optically active acid for optical resolution of compound (5) in which $R^4$ is benzyl, $R^1$ is methyl, and n is 2, and the compounds isolated through racemic resolution by use of mandelic acid are the following compounds.

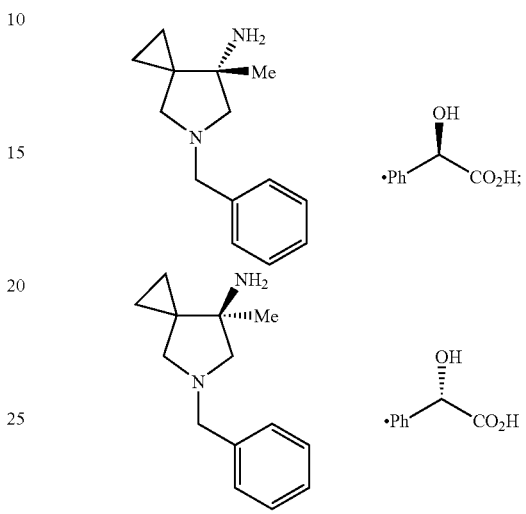

These compounds may be a hydrate thereof.

Free-form compound (5-1) or (5-2) can be recovered without lowering its optical purity through the following procedure: treating the thus-formed salt of the optically active carboxylic acid or sulfonic acid with an aqueous alkaline solution such as an aqueous inorganic base solution (e.g., aqueous sodium hydroxide, aqueous potassium hydroxide, aqueous ammonia, or aqueous sodium bicarbonate), or an aqueous organic base solution (e.g., a metal alkoxide dissolved in water) and extracting with an organic solvent which is not miscible with water such as a hydrocarbon solvent (e.g., hexane or heptane), an aromatic hydrocarbon solvent (e.g., benzene or toluene), a halo-hydrocarbon solvent (e.g., methylene chloride and chloroform), or ethyl acetate.

Compound (6) represented by formula (6):

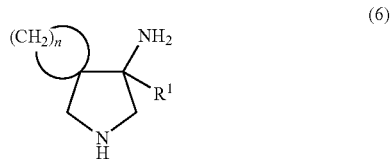

(n is an integer of 2 to 5; and $R^1$ represents a C1 to C4 alkyl group which may have a substituent or an aryl group which may have a substituent) or an optically active form thereof may be produced by removing the protective group present in the amino group in the pyrrolidine ring of compound (5) or an optically active form thereof. Removal of the protective group may be performed under known conditions depending on the type of the protective group present in the amino group. The protective group present in the amino group in the pyrrolidine ring of compound (5) is preferably a benzyl-based group from the viewpoint of easiness for the removal. Thus, compound (5) is preferably a compound (51) represented by formula (51):

(51)

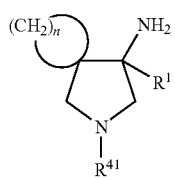

(wherein n is an integer of 2 to 5; $R^1$ represents a C1 to C4 alkyl group which may have a substituent or an aryl group which may have a substituent; and $R^{41}$ represents a benzyl group or a benzhydryl group, wherein phenyl group thereof may have, as a substituent, one or more groups selected from the group consisting of a nitro group, an alkoxy group, and a halogen atom) or an optically active form thereof. In other words, when this compound (51) is employed, hydrogenolysis readily proceeds in the presence of a metallic catalyst and in the presence of hydrogen gas or formic acid or a salt thereof as a hydrogen source, to thereby attain deprotection. In deprotection, when hydrochloric acid, hydrogen chloride dissolved in organic solvent, or the like is added to acidify the medium, reaction readily proceeds, whereby compound (6) or an optically active form thereof can be produced as a salt of the added acid.

Examples of the metallic catalyst employed in the deprotection include Raney nickel, Raney cobalt, palladium carbon, platinum carbon, and rhodium carbon. Of these, palladium carbon is preferred.

When hydrogen gas is employed, the pressure at the reaction is preferably 1 to 50 atm. When formic acid or its salt is employed as a hydrogen source, ambient pressure may be employed. Any solvent may be used in the reaction so long as the solvent does not inhibit the reaction, and an alcoholic solvent such as methanol or ethanol is preferred. The reaction can be accelerated through addition of acid to the reaction mixture. Examples of the acid include inorganic acids such as hydrochloric acid, hydrogen chloride dissolved in organic solvent, and sulfuric acid; and organic acids such as formic acid, acetic acid, and p-toluenesulfonic acid. Of these, hydrochloric acid and hydrogen chloride dissolved in organic solvent are preferred. The amount of acid is adjusted to 2 to 100 equivalents with respect to the substrate from the viewpoint of efficiency. An amount of 3 to 20 equivalents are particularly effective. In this deprotection process, stereoproperty is completely retained.

When compound represented by formula (6-1):

(6-1)

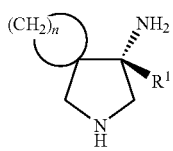

(wherein n is an integer of 2 to 5; $R^1$ represents a C1 to C4 alkyl group which may have a substituent or an aryl group which may have a substituent) or a salt thereof is reacted with a boron-chelate of a quinolone-skeleton compound represented by the following formula:

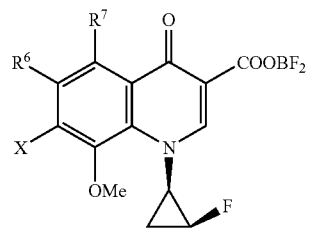

($R^6$ represents a hydrogen atom or a fluorine atom; $R^7$ represents an amino group which may have a substituent, a C1 to C4 alkoxy group which may have a substituent, a hydrogen atom, or a hydroxyl group; and X represents a leaving group) in the presence of a base, a compound represented by formula (9-1):

(9-1)

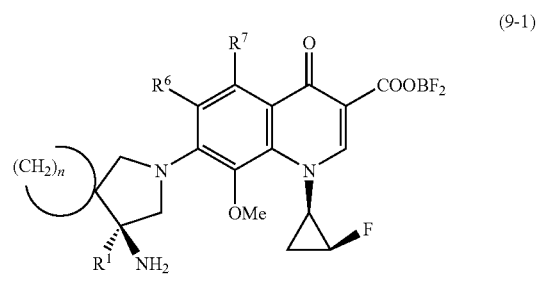

(wherein n, $R^1$, $R^6$, and $R^7$ are the same as defined above) can be produced.

The base employed in the above reaction may be an organic base or an inorganic base. Preferably, a tertiary amine as an organic amine is used. The reaction is performed in a polar solvent. Examples of the solvent include ester solvents such as ethyl acetate; amide solvents such as dimethylformamide and dimethylacetamide; acetonitrile; alcoholic solvents such as benzyl alcohol; dimethylsulfoxide; dioxolan; and 1,3-dimethyl-2-imidazolidinone. Of these, amide solvents (dimethylformamide and dimethylacetamide) are preferred. Examples of the tertiary amines employed in the reaction include trimethylamine, triethylamine, N-methylpiperidine, N-methylmorpholine, and pyridine. The reaction temperature is −20° C. to 150° C., preferably 0 to 100° C.

In the boron-chelate of a quinolone-skeleton compound, X represents a leaving group. Examples of the leaving group include a halogen atom and a substituted sulfonyloxy group. The leaving group is preferably a halogen atom, particularly a fluorine atom.

Compound represented by formula (10-1) can be produced through removing a boron-chelate moiety from a boron-chelate compound such as compound represented by formula (9-1). The removing process may be performed under basic or acidic conditions in the presence of water or a protic solvent. Depending on the employed removal conditions; i.e., basic or acidic, the compound represented by formula (10-1) may be formed as a hydrate or a salt thereof. Examples of the solvent employed for de-chelation include alcoholic solvents such as methanol, ethanol, and isopropyl alcohol; halogen-containing solvents such as chloroform; ester solvents such as ethyl acetate; and acetonitrile. Of these, alcoholic solvents such as ethanol and isopropyl alcohol are preferred. The reaction temperature is −20° C. to 150° C., preferably 0 to 100° C. Examples of the basic reagent include amine reagents such as triethylamine and pyridine; and alkali metal reagents such as sodium hydroxide and potassium hydroxide. Acidic conditions may be realized by use of an organic acid such as acetic acid, oxalic acid, or sulfonic acid; or an inorganic acid such as hydrochloric acid, sulfuric acid, or nitric acid.

Compound (7) represented by formula (7):

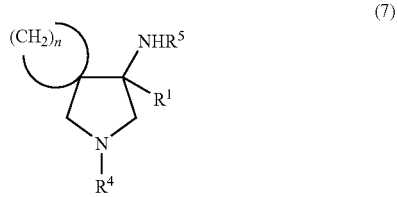

(wherein n is an integer of 2 to 5; $R^1$ represents a C1 to C4 alkyl group which may have a substituent or an aryl group which may have a substituent; $R^4$ represents a benzyl group, a benzhydryl group, or a trityl group, wherein phenyl group thereof may have, as a substituent, one or more groups selected from the group consisting of a nitro group, an alkoxy group, and a halogen atom; and $R^5$ represents a t-butyloxycarbonyl group, a benzyloxycarbonyl group, a benzoyl group, or an acetyl group) or an optically active form thereof may be produced through introducing a protective group to the primary amino group in the ring of compound (5) represented by formula (5):

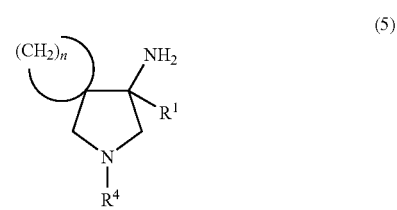

or an optically active form thereof. Examples of the protecting agent employed for introducing a protective group include di-t-butyl dicarbonate, benzoyl chloride, acetic anhydride, and acetyl chloride.

The protective group $R^4$ attached to the amino group of the ring of the compound (7) may be removed under a known removal conditions depending on the type of the protective group. For example, when the protective group is a benzyl-type protective group, the group is removed through hydrogenolysis using hydrogen gas, formic acid, or a salt thereof, as a hydrogen source, in the presence of a metallic catalyst, whereby compound (8) represented by formula (8):

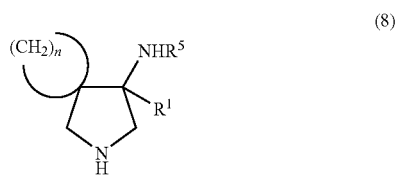

(wherein n is an integer of 2 to 5; $R^1$ represents a C1 to C4 alkyl group which may have a substituent or an aryl group which may have a substituent; and $R^5$ represents a t-butyloxycarbonyl group, a benzyloxycarbonyl group, a benzoyl group, or an acetyl group) or an optically active form thereof can be produced. The removal reaction is performed in the presence of a metallic catalyst. Examples of such a metallic catalyst include Raney nickel, Raney cobalt, palladium carbon, platinum carbon, and rhodium carbon. Of these, palladium carbon is preferred. When hydrogen gas is used, the pressure during reaction is preferably 1 to 50 atm. When formic acid or a salt thereof is used as a hydrogen source, ambient pressure may be employed. Any solvent may be used so long as it does not impede the reaction. In this deprotection process, stereoproperty is completely retained.

EXAMPLES

The present invention will hereinafter be described in detail by way of examples, which should not be construed as limiting the invention thereto.

Example 1

1-[(1-Amino-1-cyano)ethyl]-1-ethoxycarbonylcyclopropane

To a solution of 1-acetyl-1-ethoxycarbonylcyclopropane (279 g) in ethanol (1.4 L), 28% aqueous ammonia (1.4 L), ammonium chloride (478 g) and sodium cyanide (175 g) were added, and the mixture was stirred at room temperature for 16 hours. Water was added to the reaction mixture, followed by extraction with ethyl acetate. The solvent of the extract was evaporated under reduced pressure. After concentration of the extract, insoluble material was precipitated. Thus, the residue was diluted again with ethyl acetate and the insoluble material was removed through filtration. The solvent of the filtrate was evaporated under reduced pressure, to thereby yield the title product as brown oil (353 g, purity: 72.0%, yield: 78.2%).

Brown oil;

$^1$H-NMR (400 MHz, CDCl$_3$) δ ppm: 1.10-1.36 (m, 4H), 1.19 (t, J=6.8 Hz, 3H), 1.51 (s, 3H), 2.14 (brs, 2H), 4.18 (q, J=6.8 Hz, 2H).

Example 2

1-[(1-t-Butoxycarbonylamino-1-cyano)ethyl]-1-ethoxycarbonylcyclopropane

Di-t-butyl dicarbonate (25.1 g) was added to 1-[(1-amino-1-cyano)ethyl]-1-ethoxycarbonylcyclopropane (21.7 g, purity: 80.2%), and the mixture was stirred at an external temperature of 100° C. for 6 hours. The reaction mixture was cooled to room temperature, and 7N ammonia-methanol solution (4.1 mL) was added to the cooled mixture, followed by stirring for 10 minutes. The solvent was evaporated under reduced pressure, to thereby yield a crude product of the title compound as brown solid. The crude product can be purified through silica gel column chromatography (hexane ethyl acetate).

$^1$H-NMR (400 MHz, CDCl$_3$) δ ppm: 1.19-1.26 (m, 1H), 1.25 (t, J=6.8 Hz, 3H), 1.34-1.48 (m, 2H), 1.47 (s, 9H), 1.55-1.60 (m, 1H), 1.88 (s, 3H), 4.15 (q, J=6.8 Hz, 2H) 5.70 (brs, 1H).

Example 3

1-[(1-Benzoylamino-1-cyano)ethyl]-1-ethoxycarbonylcyclopropane

1-[(1-Amino-1-cyano)ethyl]-1-ethoxycarbonylcyclopropane (1.91 g, purity: 91.5%) was dissolved in acetonitrile (19 mL), and triethylamine (2.92 mL) and benzoyl chloride (2.43 mL) were added to the solution, followed by stirring at room temperature for 1 hour. After completion of reaction, water was added to the reaction mixture, and the mixture was extracted with ethyl acetate. The organic layer was dried over sodium sulfate anhydrate. The solvent of the organic layer was evaporated under reduced pressure, and the residue was purified through silica gel column chromatography (hexane: ethyl acetate), to thereby yield the title product as white crystals (2.08 g, yield: 75.6%).

$^1$H-NMR (400 MHz, CDCl$_3$) δ ppm: 1.25 (t, J=6.8 Hz, 3H), 1.30-1.36 (m, 1H), 1.40-1.44 (m, 1H), 1.52-1.58 (m, 1H), 1.75-1.80 (m, 1H), 2.00 (s, 3H), 4.15 (m, 2H), 7.43 (t, J=7.2 Hz, 2H), 7.54 (t, J=7.2 Hz, 1H), 7.81 (d, J=7.2 Hz, 2H).

Example 4

7-t-Butoxycarbonylamino-4-oxo-7-methyl-5-azaspiro[2.4]heptane

Raney nickel (17.4 mL) was added to a solution of crude 1-[(1-t-butoxycarbonylamino-1-cyano)ethyl]-1-ethoxycarbonylcyclopropane in methanol (348 mL). A reaction vessel was purged with hydrogen gas. The reaction mixture was placed in the reaction vessel, followed by stirring at an external temperature of 55° C. for 20 hours. Then, the reaction vessel was purged with nitrogen, and insoluble material was removed through filtration, followed by washing with methanol. The filtrate and the washings were combined, and the solvent of the mixture was evaporated under reduced pressure. Subsequently, isopropyl ether mL) was added to the residue, followed by stirring for 30 minutes. The thus-precipitated crystals were collected and dried under reduced pressure, to thereby yield the title product as white crystals (9.99 g).

$^1$H-NMR (400 MHz, DMSO-d$_6$) δ ppm: 0.65-0.84 (m, 4H), 1.17 (s, 3H), 1.37 (s, 9H), 3.11 (d, J=9.6 Hz, 1H), 4.11 (brd, J=9.6 Hz, 1H), 6.60 (brs, 1H), 7.59 (brs, 1H).

Example 5

7-t-Butoxycarbonylamino-4-oxo-7-methyl-5-azaspiro[2.4]heptane

Di-t-butyl dicarbonate (17.9 g) was added to 1-[(1-amino-1-cyano)ethyl]-1-ethoxycarbonylcyclopropane (16.0 g, purity: 72.0%), and the mixture was stirred at an external temperature of 100° C. for 6 hours. The reaction mixture was cooled to room temperature, and 7N ammonia-methanol solution (4.5 mL) was added to the cooled mixture, followed by stirring for 10 minutes. Subsequently, the solvent of the reaction mixture was evaporated under reduced pressure, to thereby yield crude 1-[(1-t-butoxycarbonylamino-1-cyano)ethyl]-1-ethoxycarbonylcyclopropane (19.23 g) as brown oil (gradually solidified). Subsequently, 5% rhodium carbon (5.06 g) was added to a solution of the crude product (18.68 g) in methanol (202 mL). A reaction vessel was purged with hydrogen gas, and the reaction mixture placed in the reaction vessel was stirred at an external temperature of 55° C. for 38 hours. Then, the reaction vessel was purged with nitrogen gas, and methanol (260 mL) was added to the reaction mixture placed in the reaction vessel. The reaction mixture was stirred at an external temperature of 55° C. for 1 hour, and insoluble material was removed through filtration. The solvent of the filtrate was evaporated under reduced pressure, and isopropyl ether (348 mL) was added to the residue, followed by stirring for 30 minutes. The precipitated crystals were collected through filtration, and dried under reduced pressure, to thereby yield the title product as white crystals (9.99 g, yield: 74.9% with respect to 1-[(1-amino-1-cyano)ethyl]-1-ethoxycarbonylcyclopropane).

Example 6

7-Benzoylamino-4-oxo-7-methyl-5-azaspiro[2.4]heptane

1-[(1-Benzoylamino-1-cyano)ethyl]-1-ethoxycarbonylcyclopropane (1.00 g, 3.49 mmol) was dissolved in ethanol, and Raney nickel (10 mL) was added to the solution, followed by stirring in a hydrogen gas atmosphere at room temperature. After four hours, insoluble material was removed through filtration, and the filtrate was concentrated under reduced pressure, to thereby yield the title product as crude white crystals (756 mg, yield: 88.6%).

$^1$H-NMR (400 MHz, CD$_3$OD) δ ppm: 0.86-0.99 (m, 2H), 1.06-1.12 (m, 2H), 1.43 (s, 3H), 3.41 (d, J=10.2 Hz, 1H), 4.11 (d, J=10.2 Hz, 1H), 7.43 (t, J=6.8 Hz, 2H), 7.49 (t, J=6.8 Hz, 1H), 7.74 (d, J=6.8 Hz, 2H).

Example 7

5-Benzyl-7-t-butoxycarbonylamino-4-oxo-7-methyl-5-azaspiro[2.4]heptane 7-t-Butoxycarbonylamino-4-oxo-7-methyl-5-azaspiro[2.4]heptane (42.63 g) was suspended in dimethylformamide (850 mL) under a nitrogen gas atmosphere, and the suspension was cooled with ice. To the suspension, 60% sodium hydride (6.93 g) was added, and the mixture was returned to room temperature. Subsequently, benzyl bromide (22.64 mL) was added to the reaction mixture, followed by stirring. After three hours, insoluble material was removed through filtration, and water was added to the filtrate. Ethyl acetate was further added thereto for extraction. The organic layer obtained through extraction was dried with sodium sulfate, followed by filtration. The filtrate was concentrated under reduced pressure, to thereby yield an oily residue. The residue was subjected to silica gel chromatography (hexane:ethyl acetate), to thereby yield the title product as pale yellow oil (51.0 g, yield: 89.2%).

$^1$H-NMR (400 MHz, CDCl$_3$) δ ppm: 0.77-0.81 (m, 1H), 0.92-1.05 (m, 2H), 1.22 (s, 3H), 1.20-1.26 (m, 1H), 1.37 (s, 9H), 3.14 (d, J=10.4 Hz, 1H), 3.98 (brd, J=10.4 Hz, 1H), 4.43 (d, J=14.8 Hz, 1H), 4.56 (d, J=14.8 Hz, 1H), 4.57 (brs, 1H), 7.22-7.34 (m, 5H).

Example 8

7-Amino-5-benzyl-4-oxo-7-methyl-5-azaspiro[2.4]heptane

5-Benzyl-7-t-butoxycarbonylamino-4-oxo-7-methyl-5-azaspiro[2.4]heptane (43.63 g) was dissolved in toluene, and the solution was stirred under ice-cooling. 37% Concentrated hydrochloric acid (100 mL) was added dropwise thereto, followed by stirring. After 0.5 hours, water was added to the reaction mixture. The mixture was stirred and left to stand so as to separate the aqueous layer from the organic layer. Sodium hydroxide (54 g) was added to and dissolved in the separated aqueous layer so as to alkalify the layer. The aqueous layer was extracted several times with toluene repeatedly. All the toluene layers were combined and washed with saturated brine. The washed toluene layer was dried with sodium sulfate, followed by filtration. The filtrate was concentrated under reduced pressure, to thereby yield the title product (21.29 g, yield: 90.2%).

$^1$H-NMR (400 MHz, CDCl$_3$) δ ppm: 0.72-0.84 (m, 2H), 0.99-1.13 (m, 2H), 1.06 (s, 3H), 3.11 (d, J=9.6 Hz, 1H), 3.22 (d, J=9.6 Hz, 1H), 4.48 (d, J=15.2 Hz, 1H), 4.52 (d, J=15.2 Hz, 1H), 7.21-7.38 (m, 5H).

Example 9

7-Amino-5-benzyl-4-oxo-7-methyl-5-azaspiro[2.4]heptane

A suspension of 7-t-butoxycarbonylamino-4-oxo-7-methyl-5-azaspiro[2.4]heptane (10.0 g, 41.6 mmol) in dimethylacetamide (100 mL) was cooled with ice, and t-butoxy potassium (4.67 g, 1.0 eq.) and benzyl chloride (5.27 mL, 1.1 eq.) were added thereto. The reaction mixture was returned to room temperature, followed by stirring for 2 hours. Thereafter, water was added to the mixture, followed by extraction with toluene. The solvent of the extract was evaporated under reduced pressure, to thereby yield 5-benzyl-7-t-butoxycarbonylamino-4-oxo-7-methyl-5-azaspiro[2.4]heptane as a crude product. The crude product was dissolved in toluene (100 mL), and methanesulfonic acid (2.97 mL) was added to the solution, followed by stirring under reflux for 2 hours. The reaction mixture was cooled to room temperature. Water was added to the cooled mixture for extraction, and the formed organic layer was removed. Aqueous sodium hydroxide solution (5N) was added to the remaining aqueous layer so as to alkalify the layer, followed by extraction with toluene. The solvent of the extract was evaporated under reduced pressure, to thereby yield the title product as a pale brown solid (8.63 g, yield: 90.1%).

Example 10

7-Amino-5-benzyl-7-methyl-5-azaspiro[2.4]heptane

7-Amino-5-benzyl-4-oxo-7-methyl-5-azaspiro[2.4]heptane (27 g) was dissolved in anhydrous tetrahydrofuran (265 mL) in an argon atmosphere, and the solution was cooled with ice. Lithium aluminum hydride (13.3 g) was added thereto, and the mixture was returned to room temperature. After disappearance of the starting materials had been confirmed, the reaction mixture was cooled with ice. Water (200 mL) and 28% aqueous sodium hydroxide solution (70 mL) were added to cooled mixture, followed by stirring. Toluene was added to the mixture for extraction to separate the organic layer, and the organic layer was washed with saturated brine, followed by drying with sodium sulfate. The desiccant was removed through filtration, and the filtrate was concentrated under reduced pressure, to thereby yield the title product (24.7 g, yield: 98.6%).

Pale yellow oil;
$^1$H-NMR (400 MHz, CDCl$_3$) δ ppm: 0.36-0.45 (m, 2H), 0.53-0.66 (m, 2H), 0.95 (s, 3H), 1.40 (brs, 2H), 2.47 (d, J=9.2 Hz, 1H), 2.55 (d, J=9.2 Hz, 1H), 2.74 (dd, J=9.2, 1.2 Hz, 2H), 3.58 (d, J=13.2 Hz, 1H), 3.62 (d, J=13.2 Hz, 1H), 7.21-7.39 (m, 5H).

Example 11

7-Amino-5-benzyl-7-methyl-5-azaspiro[2.4]heptane

A solution (65% toluene solution) of sodium bis(2-methoxyethoxy)aluminum hydride (1.65 kg, 3.5 eq.) in toluene (870 mL) was added to a solution of 7-amino-5-benzyl-4-oxo-7-methyl-5-azaspiro[2.4]heptane (348 g, 1.51 mmol) in toluene (2.62 L), and the mixture was stirred at an internal temperature of 60° C. for 1 hour. The reaction mixture was cooled with ice. Aqueous sodium hydroxide solution (5N) was added to the cooled mixture, and the aqueous layer was extracted with toluene. The thus-obtained organic layers were combined, and the solvent of the combined organic layer was evaporated under reduced pressure, to thereby yield the title product as brown oil (343 g, purity: 81.3%, yield: 100%).

Example 12

(−)-7-Amino-5-benzyl-7-methyl-5-azaspiro[2.4]heptane D-mandelate

D-Mandelic acid (111 g) was added to a solution of 7-amino-5-benzyl-7-methyl-5-azaspiro[2.4]heptane (325 g, purity: 81.3%, 1.22 mol) in toluene (4.8 L), and seed crystals for the title compound were added to the mixture, followed by stirring overnight (for 20 hours) at an internal temperature of −9° C. The precipitated crystals were collected through filtration, followed by washing twice with cold toluene (400 mL) and drying under reduced pressure, to thereby yield the title product as white crystals (117 g, yield: 26.0%, optical purity: 99.2% e.e.). Optical purity of the product was determined through HPLC. Specifically, the mandelate (about 10 mg) was sampled, and 10% aqueous sodium hydroxide (0.3 mL) and hexane (0.3 mL) were added to the sampled mandelate. After stirring, the mixture was left to stand, and the hexane layer was analyzed through HPLC. The $^1$H-NMR spectral data given below were obtained from the free form of the product.

HPLC Conditions:
Column: DAICEL CHIRALPAK OD-H, 0.46×150 mm
Column temperature: 30° C.
Mobile phase: n-hexane:isopropyl alcohol=95:5, flow rate: 1.0 mL/min
Wavelength: 254 nm, (−) form: 8.7 min, (+) form: 7.4 min
The peak at 8.7 min is, among others, a predominant peak and is attributed to an antipode obtained through racemic resolution with D-mandelic acid.

$^1$H-NMR (400 MHz, CDCl$_3$) δ ppm: 0.32-0.38 (m, 1H), 0.44-0.50 (m, 1H), 0.60-0.66 (m, 1H), 0.79-0.85 (m, 1H), 0.91 (s, 3H), 2.41-2.46 (m, 2H), 2.82 (d, J=9.2 Hz, 1H), 2.99 (d, J=9.2 Hz, 1H), 3.57 (d, J=12.8 Hz, 2H), 3.71 (d, J=12.8 Hz, 1H), 4.67 (brs, 1H), 4.86 (s, 1H), 7.16-7.42 (m, 10H). Optical rotation $[α]_D$=−69.9° (c=1.0, MeOH)

Example 13

(−)-7-Amino-5-benzyl-7-methyl-5-azaspiro[2.4]heptane D-(−)-mandelate

Toluene (11.5 L) was added to a solution (1,660 mL) of 7-amino-5-benzyl-7-methyl-5-azaspiro[2.4]heptane (2,202 g, purity: 35%) in toluene, and D-mandelic acid (325.2 g) was added to the mixture, followed by cooling. Seed crystals for the title compound were added to the cooled mixture, followed by stirring overnight at an internal temperature of −10° C. The precipitated crystals were collected through filtration and washed twice with cold toluene, followed by drying under reduced pressure. The thus-obtained crude products (first crude crystals) were suspended under stirring in toluene (2.2 L) at room temperature. After 2.5 hours, the suspension was filtered so as to collect crystals. The collected crystals were washed with cold toluene, followed by drying under reduced pressure, to thereby yield the title product as white crystals (first crystals) (365.4 g, yield: 27.1%, optical purity: 97.4% e.e.).

To the toluene-containing filtrate remaining after first crude crystals had been collected, 10% aqueous sodium hydroxide was added, and the mixture was stirred at room temperature, followed by separation of the organic layer. In addition, saturated brine was added to the organic layer so as to separate another organic layer, followed by drying with sodium sulfate. The desiccant was removed through filtration, and the filtrate was concentrated under reduced pressure. Subsequently, toluene (13.5 L) was added to the concentration residue, and L-mandelic acid (297.5 g) was added to the mixture, followed by cooling. Seed crystals for the title compound were added to the cooled mixture, and the mixture was stirred overnight at an internal temperature of –8° C. The precipitated crystals were collected through filtration, to thereby yield (+)-7-amino-5-benzyl-7-methyl-5-azaspiro[2.4]heptane L-mandelate (512.7 g, optical purity: 97.0% e.e.). Thereafter, the mother liquid was concentrated to form a residue (542.7 g). Toluene (4.9 L) was added to the residue, and D-mandelic acid (125 g) was added to the mixture, followed by cooling. Seed crystal for the title compound was added to the cooled mixture, and the mixture was stirred overnight at an internal temperature of –9° C. The precipitated crystals were collected through filtration and washed with cold toluene. In addition, the washed crystals were suspended under stirring in hexane (600 mL) at room temperature. After 2.5 hours, the suspension was filtered. The collected crystals were dried under reduced pressure, to thereby yield the title product as white crystals (second crystals) (185.5 g, yield: 13.7%, optical purity: 97.4% e.e.).

(+)-7-Amino-5-benzyl-7-methyl-5-azaspiro[2.4] heptane L-mandelate

A free-form amine was produced from the thus-obtained salt and was subjected to $^1$H-NMR measurement. The spectrum of the amine was found to coincide with that of the free-form compound of Example 12.

White powdery crystals;
Optical rotation $[\alpha]_D$=+65.6° (c=1.0, MeOH)

Example 14

(–)-7-Amino-5-benzyl-7-methyl-5-azaspiro[2.4] heptane

To (–)-7-amino-5-benzyl-7-methyl-5-azaspiro[2.4]heptane D-mandelate (22.43 g, optical purity: 98% e.e.), 10% Aqueous sodium hydroxide and toluene were added, and the mixture was stirred at room temperature. Thereafter, the toluene layer was separated, washed with saturated brine, and dried with sodium sulfate. The desiccant was removed through filtration, and the filtrate was concentrated under reduced pressure, to thereby yield the title product as pale yellow oil (16.13 g, optical purity: 98% e.e.).

Pale yellow oil;
$^1$H-NMR (400 MHz, CDCl$_3$) δ ppm: 0.36-0.45 (m, 2H), 0.53-0.66 (m, 2H) 0.95 (s, 3H), 1.43 (brs, 2H), 2.47 (d, J=9.2 Hz, 1H), 2.55 (d, J=9.2 Hz, 1H), 2.735 (d, J=9.2 Hz, 1H), 2.740 (d, J=9.2 Hz, 1H), 3.58 (d, J=13.2 Hz, 1H), 3.62 (d, J=13.2 Hz, 1H), 7.21-7.39 (m, 5H)

Optical rotation $[\alpha]_D$=–25.6° (c=1.1, MeOH)

Example 15

(+)-7-Amino-5-benzyl-7-methyl-5-azaspiro[2.4] heptane (+)-7-Amino-5-benzyl-7-methyl-5-azaspiro[2.4]heptane L-mandelate (6.16 g, optical purity: 96% e.e.) was processed in a manner similar to that employed in Example 14, to thereby form a target product (7.99 g, purity: 47%, optical purity: 96% e.e.) as pale yellow oil. $^1$H-NMR data of the product were found to coincide with those obtained in Example 14.

Optical rotation $[\alpha]_D$=+22.1° (c=1.1, MeOH)

Example 16

(–)-7-Amino-7-methyl-5-azaspiro[2.4]heptane dihydrochloride

Methanol (91 mL) was added to (–)-7-amino-5-benzyl-7-methyl-5-azaspiro[2.4]heptane (16.2 g) for dissolution. To the solution, 5% palladium carbon (5.33 g, water content: 50%) and concentrated hydrochloric acid (15.8 mL) were added. A reaction vessel was purged with hydrogen gas, and the mixture placed in the reaction vessel was stirred for 13 hours. The catalyst was removed through filtration and washing with ethanol. All the organic layers were combined and concentrated under reduced pressure. Ethanol and isopropyl alcohol were added to the residue, and the mixture was concentrated under reduced pressure several times under azeotropic conditions. After azeotropy, isopropyl alcohol was added to the residue, and the mixture was stirred at room temperature so as to precipitate crystals. The crystals were collected through filtration and dried under reduced pressure, to thereby yield first crystals of the title compound (9.75 g, yield: 80%). Through elemental analysis, the obtained first crystals were found to be a dihydrochloride salt. To another residue obtained through concentration of the filtrate, methanol and isopropyl alcohol were added, and the mixture was cooled so as to precipitate crystals. The crystals were collected through filtration and dried under reduced pressure, to thereby yield second crystals of the title compound (1.41 g, yield: 12%).

$^1$H-NMR (400 MHz, D$_2$O) δ ppm: 0.73-0.78 (m, 1H), 0.89-1.01 (m, 3H), 1.40 (s, 3H), 3.25 (d, J=12.8 Hz, 1H), 3.61 (d, J=12.8 Hz, 1H), 3.62 (d, J=13.6 Hz, 1H), 3.74 (d, J=13.6 Hz, 1H).

Elemental analysis: as C$_7$H$_{14}$N$_2$.2HCl;
Calculated: C, 42.22; H, 8.10; N, 14.07; Cl, 35.61.
Found: C, 41.92; H, 8.27; N, 13.79; Cl, 35.21.
Optical rotation $[\alpha]_D$=–11° (c=1.0, H$_2$O)

Example 17

(–)-7-Amino-7-methyl-5-azaspiro[2.4]heptane dihydrochloride

To a solution of (–)-7-amino-5-benzyl-7-methyl-5-azaspiro[2.4]heptane D-(–)-mandelate (94.0 g, 255 mmol) in toluene (940 mL), 1N aqueous sodium hydroxide (470 mL) was added, and the mixture was stirred for 10 minutes. The toluene layer was separated and concentrated under reduced pressure. The residue was dissolved in methanol (940 mL), and concentrated hydrochloric acid (64 mL) and 5% palladium carbon (9.40 g) were added to the solution. A reaction vessel was purged with hydrogen gas, and the reaction mixture placed in the reaction vessel was stirred at room temperature for 19 hours. After completion of reaction, the reaction mixture was filtered through Celite so as to remove insoluble material, followed by washing twice with methanol. The filtrate and the washings were combined, and the solvent of the mixture was evaporated under reduced pressure. Thereafter, isopropyl alcohol was added to the residue, and the mixture was stirred overnight at room temperature and further stirred for 2 hours with ice-cooling. The precipitated crystals were collected through filtration and washed with cold isopropyl alcohol, followed by drying under reduced pressure, to thereby yield first crystals of the title compound as pale brown crystals (47.3 g, yield: 93.0%). Second crystals of the title compound (1.37 g, 2.7%) were also collected from the filtrate.

Example 18

(+)-7-Amino-7-methyl-5-azaspiro[2.4]heptane dihydrochloride (+)-7-amino-5-benzyl-7-methyl-5-azaspiro[2.4]heptane (2.1 g, optical purity: 98% e.e.) was processed in a manner similar to that employed in Example 16, to thereby form a target product (1.09 g). $^1$H-NMR data of the product were found to coincide with those obtained in Example 16.

Optical rotation $[\alpha]_D$=+11.2° (c=1.0, H$_2$O)

Example 19

5-Benzyl-7-t-butoxycarbonylamino-7-methyl-5-azaspiro[2.4]heptane

7-Amino-5-benzyl-7-methyl-5-azaspiro[2.4]heptane (7.3 g) was dissolved in toluene (30 mL) t-Butyl dicarbonate (9.3 mL) and 1N aqueous sodium hydroxide (10 mL) were added to the solution, followed by stirring for 15 hours at room temperature and then for 4 hours at 50° C. After completion of reaction, the toluene layer was separated and washed with water, followed by drying with sodium sulfate. The desiccant was removed through filtration, and the filtrate was concentrated under reduced pressure. The residue was purified through silica gel chromatography (hexane:ethyl acetate), to thereby yield the title product (8.745 g, yield: 82%). Notably, when optically active 7-amino-5-benzyl-7-methyl-5-azaspiro[2.4]heptane is treated in accordance with the above-described procedure, the corresponding optically active target product can be yielded without decreasing optical purity.

White crystals;
$^1$H-NMR (400 MHz, CDCl$_3$) δ ppm: 0.41-0.45 (m, 1H), 0.50-0.55 (m, 1H), 0.64-0.69 (m, 1H), 0.80-0.85 (m, 1H), 1.20 (s, 3H), 1.43 (s, 9H), 2.43 (d, J=9.2 Hz, 1H), 2.58 (d, J=9.6 Hz, 1H), 2.83 (d, J=9.2 Hz, 1H), 3.32 (d, J=9.6 Hz, 1H), 3.57 (d, J=13.2 Hz, 1H), 3.68 (d, J=13.2 Hz, 1H), 4.75 (brs, 1H), 7.22-7.38 (m, 5H).

Example 20

(−)-7-t-Butoxycarbonylamino-7-methyl-5-azaspiro[2.4]heptane (−)-7-Amino-5-benzyl-7-methyl-5-azaspiro[2.4]heptane D-mandelate (5.99 g) was dissolved in toluene (60 mL). To the solution, 5N Aqueous sodium hydroxide (60 mL) was added, and the mixture was stirred at room temperature, followed by separation of the toluene layer. Toluene was also added to the remaining aqueous layer for extraction. All the toluene layers were combined, and t-butyl dicarbonate (19.0 mL) was added to the combined toluene layer, followed by stirring at room temperature for 2 hours. After completion of reaction, 10% aqueous citric acid was added to the reaction mixture, to thereby extract the aqueous citric acid layer. Separately, 10% aqueous citric acid was added to the remaining toluene layer, to thereby separate another aqueous citric acid layer. Thereafter, all the aqueous layers were combined, and the combined aqueous layer was alkalified with 5N aqueous sodium hydroxide (30 mL). Subsequently, toluene was added to the alkalified aqueous layer so as to extract the organic layer, and the solvent of the organic layer obtained through extraction was evaporated under reduced pressure. Methanol (60.0 mL) was added to the residue, and 5% palladium carbon (0.59 g, water content: 50%) was added to the mixture, followed by stirring at room temperature in a hydrogen atmosphere. After 14 hours, 5% palladium carbon was removed through filtration. The filtrate was concentrated under reduced pressure, to thereby yield the title product (3.576 g, yield: 97%). This product can be purified through recrystallization from a solvent such as hexane, heptane, or acetonitrile, or formation of a crystalline salt with, for example, oxalic acid.

White crystals;
$^1$H-NMR (400 MHz, CDCl$_3$) δ ppm: 0.39-0.44 (m, 1H), 0.57-0.61 (m, 2H), 0.76-0.81 (m, 1H), 1.10 (s, 3H), 1.44 (s, 9H), 1.87 (br s, 1H), 2.77 (d, J=12.0 Hz, 1H), 2.78 (d, J=11.2 Hz, 1H), 3.14 (d, j=11.2 Hz, 1H), 3.70 (br d, J=12.0 Hz, 1H), 4.46 (br s, 1H).

Optical rotation $[\alpha]_D$=−70.1° (c=1.0, MeOH)

Example 21

7-[(7S)-7-Amino-7-methyl-5-azaspiro[2.4]heptan-5-yl]-6-fluoro-8-methoxy-1-[(1R,2S)-2-fluoro-1-cyclopropyl]-1,4-dihydro-4-oxo-3-quinolinecarboxylic acid-BF$_2$ complex 6,7-Difluoro-8-methoxy-1-[(1R,2S)-2-fluoro-1-cyclopropyl]-1,4-dihydro-4-oxo-3-quinolinecarboxylic acid-BF$_2$ complex (7.2 g) was dissolved in dimethylacetamide (22 mL). (−)-7-Amino-7-methyl-5-azaspiro[2.4]heptane dihydrochloride (4.8 g) and triethylamine (9.45 mL) were added to the solution, followed by stirring at 30° C. The reaction mixture was stirred overnight (for 18 hours), and water was added to the reaction mixture. The precipitated crystals were collected through filtration and dried, to thereby yield the title product as yellow crystals (8.25 g, yield: 89%).
$^1$H-NMR (400 MHz, CD$_3$OD) δ ppm: 0.56-0.64 (m, 2H), 0.79-0.90 (m, 2H), 1.20 (s, 3H), 1.65-1.78 (m, 2H), 3.68 (s, 3H), 3.80-3.94 (m, 4H), 4.31-4.38 (m, 1H), 5.00 (dm, J=65.6 Hz, 1H), 7.86 (d, J=14.0, 1H), 9.08 (d, J=2.0 Hz, 1H).

Example 22

7-[(7R)-7-Amino-7-methyl-5-azaspiro[2.4]heptan-5-yl]-6-fluoro-8-methoxy-1-[(1R,2S)-2-fluoro-1-cyclopropyl]-1,4-dihydro-4-oxo-3-quinolinecarboxylic acid-BF$_2$ complex 6,7-Difluoro-8-methoxy-1-[(1R,2S)-2-fluoro-1-cyclopropyl]-1,4-dihydro-4-oxo-3-quinolinecarboxylic acid-BF$_2$ complex (1.19 g) was dissolved in dimethylacetamide (3.6 mL). (+)-7-Amino-7-methyl-5-azaspiro[2.4]heptane dihydrochloride (0.72 g) and triethylamine (1.47 mL) were added to the solution, followed by stirring at 35° C. for 4 hours. The reaction mixture was further stirred at room temperature overnight (for 18 hours), and water was added thereto. The precipitated crystals were collected through filtration and dried, to thereby yield the title product as yellow crystals (1.31 g, yield: 85.0%).

$^1$H-NMR (400 MHz, DMSO-D$_6$) δ ppm: 0.41-0.64 (m, 3H), 0.75-0.83 (m, 1H), 1.10 (s, 3H), 1.53-1.82 (m, 2H), 3.60 (s, 3H), 3.67-3.85 (m, 4H), 4.29-4.36 (m, 1H), 5.09 (dm, J=64.0 Hz, 1H), 7.83 (d, J=14.0, 1H), 9.00 (d, J=2.4 Hz, 1H).

Example 23

7-[(7S)-7-Amino-7-methyl-5-azaspiro[2.4]heptan-5-yl]-6-fluoro-8-methoxy-1-[(1R,2S)-2-fluoro-1-cyclopropyl]-1,4-dihydro-4-oxo-3-quinolinecarboxylic acid Isopropyl alcohol (16.4 mL), water (7.0 mL), and triethylamine (1.39 mL) were added to crude 7-[(7S)-7-amino-7-methyl-5-azaspiro[2.4]heptan-5-yl]-6-fluoro-8-methoxy-1-[(1R,2S)-2-fluoro-1-cyclopropyl]-1,4-dihydro-4-oxo-3-quinolinecarboxylic acid-BF$_2$ complex (4.67 g). The mixture was stirred for 3 hours under heating at 80° C. Thereafter, the mixture was cooled to room temperature, and the precipitated crystals were collected through filtration, followed by drying, to thereby yield a crude product of the title compound (4.14 g, yield: 98.7%). The crude product (0.20 g) was recrystallized from acetonitrile (2.2 mL), to thereby yield the title product as pale yellow crystals (0.135 g, yield: 67.5%).

$^1$H-NMR (400 MHz, DMSO-D$_6$) δ ppm: 0.39-0.60 (m, 3H), 0.76-0.81 (m, 1H), 1.09 (s, 3H), 1.52-1.65 (m, 2H), 3.49-3.81 (m, 4H), 3.59 (s, 3H), 4.05-4.12 (m, 1H), 4.85-5.07 (m, 1H), 7.66 (d, J=14.0, 1H), 8.67 (d, J=1.6 Hz, 1H).

Separately, the crude product was suspended in isopropyl alcohol (about 20-fold volume with respect to weight of the crude product), and concentrated hydrochloric acid (about 1.5-fold volume with respect to weight of the crude product) was added to the suspension, followed by stirring and filtering, to thereby yield a hydrochloric acid salt of the title compound.

Theoretically, the compound produced in Example 23 may include two isomers in terms of the coordination mode of the amino group and the methyl group attached to the carbon atom to which the amino group of the spiropyrrolidinyl group which serves as a 7-position substituent is bound. The quinolone compound produced in Example 23 was found to be an isomer thereof exhibiting higher antibacterial effect. Therefore, the stereoconfiguration of the amine compound produced through racemic resolution in Example 12 was found to be the coordination mode of the amino group and the methyl group for attaining more potent antibacterial effect.

Example 24

7-[(7R)-7-Amino-7-methyl-5-azaspiro[2.4]heptan-5-yl]-6-fluoro-8-methoxy-1-[(1R,2S)-2-fluoro-1-cyclopropyl]-1,4-dihydro-4-oxo-3-quinolinecarboxylic acid Isopropyl alcohol (2.1 mL), water (0.9 mL), and triethylamine (0.18 mL) were added to crude 7-[(7R)-7-amino-7-methyl-5-azaspiro[2.4]heptan-5-yl]-6-fluoro-8-methoxy-1-[(1R,2S)-2-fluoro-1-cyclopropyl]-1,4-dihydro-4-oxo-3-quinolinecarboxylic acid-BF$_2$ complex (0.60 g). The mixture was stirred for 3 hours under heating at 80° C. Thereafter, the mixture was cooled to room temperature. The precipitated crystals were collected through filtration and dried, to thereby yield a crude product of the title compound (0.51 g, yield: 95.1%). This crude product (0.30 g) was recrystallized from acetonitrile (3.0 mL), to thereby yield the title product as pale yellow crystals (0.20 g, yield: 66.7%).

$^1$H-NMR (400 MHz, DMSO-D$_6$) δ ppm: 0.39-0.60 (m, 3H), 0.70-0.80 (m, 1H), 1.09 (s, 3H), 1.47-1.59 (m, 2H), 3.51-3.79 (m, 4H), 3.57 (s, 3H), 4.03-4.11 (m, 1H), 4.93-5.15 (m, 1H), 7.66 (d, J=14.4, 1H), 8.63 (d, J=2.4 Hz, 1H).

Referential Example 1 t-Butyl 5-oxo-1-[(1R)-1-phenylethyl]pyrrolidine-3-carboxylate

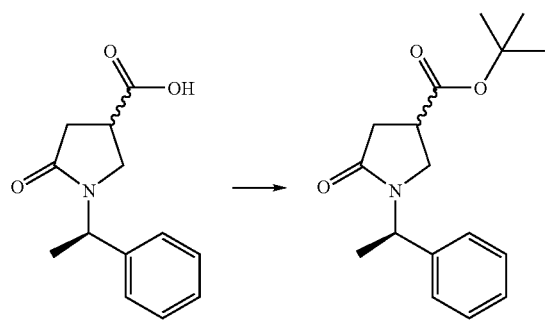

Under stirring by means of an impeller, O-t-butyl-N,N'-diisopropylurea (3,020 g, 15.00 mol) was added at room temperature to a suspension of 5-oxo-1-[(1R)-1-phenylethyl] pyrrolidine-3-carboxylic acid (1,165 g, 4.994 mol), which had been produced through the method described in the literature (i.e., Culbertson T. P., Domagala J. M., Nichols J. F., Priebe S., and Skeean R. W., J. Med. Chem., 1987, 30, 1711-1715.), in dichloromethane (10 L). After an increase in internal temperature and initiation of reflux had been confirmed, the mixture was cooled in an ice-water bath. The reaction mixture was cooled to room temperature. Thereafter, the ice-water bath was removed, and the reaction mixture was stirred for 1 hour. Subsequently, the mixture was stirred for 3 hours under heating at 40° C. The reaction mixture was stirred for 1 hour with cooling in an ice-water bath, and insoluble material was removed through filtration. The filtrate was evaporated to dryness under reduced pressure, and the residue was purified through silica gel column chromatography (silica gel: 4 kg, eluent: hexane:ethyl acetate=3:1), to thereby yield the title compound as pale yellow syrup (3-position isomer mixtures) (925.2 g, 64%). The diastereomers in terms of the 3-position of pyrrolidine can be readily fractionated. However, since the subsequent step include reaction involving epimerization, the diastereomers were used without performing fractionation. $^1$H-NMR spectral data of each diastereomer, which had been separately fractionated, are given below.

Low-Polar Isomer:

$^1$H-NMR (400 MHz, CDCl$_3$) δ ppm: 1.45 (9H, s), 1.54 (3H, d, J=7.08 Hz), 2.59-2.74 (2H, m), 2.95-3.03 (1H, m), 3.14 (1H, dd, J=9.77, 8.79 Hz), 3.49 (1H, dd, J=9.77, 6.35 Hz), 7.26-7.36 (5H, m).

High-Polar Isomer $^1$H-NMR (400 MHz, CDCl$_3$) δ ppm: 1.36 (9H, s), 1.53 (3H, d, J=7.32 Hz), 2.59-2.75 (2H, m), 3.02-3.11 (1H, m), 3.16 (1H, dd, J=10.01, 5.62 Hz), 3.51 (1H, dd, J=10.01, 8.54 Hz), 7.24-7.36 (5H, m). :

Referential Example 2 t-Butyl (3S)-3-methyl-5-oxo-1-[(1R)-1-phenylethyl]pyrrolidine-3-carboxylic acid

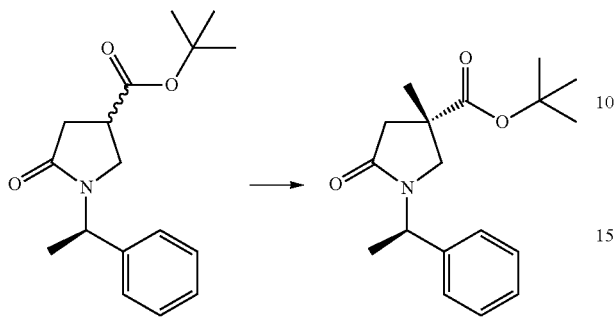

Under a nitrogen gas atmosphere, iodomethane (26.0 mL, 59.28 g, 0.418 mol) and sodium hydride (oil content: 55%, 11.35 g, 0.260 mol) were sequentially added at room temperature to a solution of t-butyl 5-oxo-1-[(1R)-1-phenylethyl]pyrrolidine-3-carboxylic acid (30.05 g, 0.104 mol) in N,N'-dimethylformamide (210 mL) with stirring. When the internal temperature reached to about 50° C., the mixture was cooled to 30° C. in an ice-water bath. Subsequently, the bath was changed to a water bath having an external temperature of 17° C., followed by stirring for 23 hours. The reaction mixture was poured into cold aqueous citric acid (a mixture of 10% citric acid (1 L) and ice (500 g)), followed by stirring for 30 minutes and extracting with ethyl acetate (800 mL, 500 mL). The organic layers were combined. The combined organic layer was washed with saturated brine, followed by drying over sodium sulfate anhydrate and filtration. The filtrate was evaporated to dryness under reduced pressure. The residue was purified through flash silica gel column chromatography (eluent; hexane:ethyl acetate=5:1 to 4:1),to thereby yield the title compound as white solid (10.63 g, 33.7%) as a high-polar isomer. In addition, t-butyl (3R)-3-methyl-5-oxo-1-[(1R)-1-phenylethyl]pyrrolidine-3-carboxylic acid (14.91 g, 47.3%) was produced as a low-polar isomer.

$^1$H-NMR (400 MHz, CDCl$_3$) δ ppm: 1.34 (12H, s), 1.52 (3H, d, J=7.10 Hz), 2.27 (1H, d, J=17.0 Hz), 2.93 (1H, d, J=17.0 Hz), 3.05 (1H, d, J=10.1 Hz), 3.32 (1H, d, J=10.1 Hz), 5.50 (1H, q, J=7.1 Hz), 7.23-7.38 (5H, m).

Referential Example 3 t-Butyl (3S)-4-[2-(t-butyldimethylsilyl)hydroxyethyl]-3-methyl-5-oxo-1-[(1R)-phenylethyl]pyrrolidine-3-carboxylate

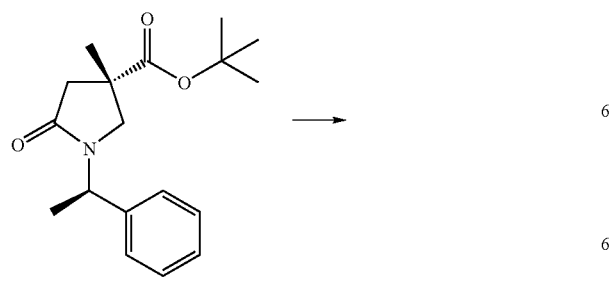

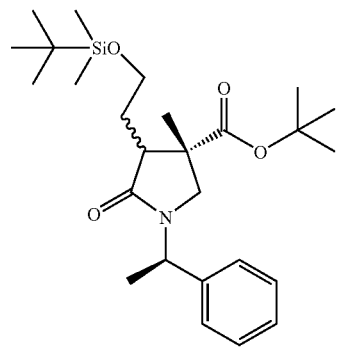

t-Butyl (3S)-3-methyl-5-oxo-1-[(1R)-phenylethyl]pyrrolidine-3-carboxylate (30.0 g, 98.9 mmol) and t-butyl (2-iodoethoxy)dimethylsilane (36.8 g, 129 mmol) were dissolved in anhydrous tetrahydrofuran (288 mL), and lithium bis(trimethylsilyl)amide (1.0M tetrahydrofuran solution, 129 mL, 129 mmol) was added dropwise to the solution at −4° C., followed by stirring at 2° C. for 3.5 hours. Subsequently, saturated aqueous ammonium chloride solution (300 mL) was added to the reaction mixture, followed by extraction with ethyl acetate (300 mL, 200 mL). The thus-obtained organic layer was washed with saturated brine (200 mL), followed by drying over sodium sulfate anhydrate and filtration. The filtrate was evaporated to dryness under reduced pressure, to thereby yield the title compound (54.1 g). The thus-obtained compound was used in the next step without any purification.

MS (ESI) m/z: 363 (M-Boc+H)+.

Referential Example 4 t-Butyl (3S)-4-(2-hydroxyethyl)-3-methyl-5-oxo-1-[(1R)-phenylethyl]pyrrolidine-3-carboxylate

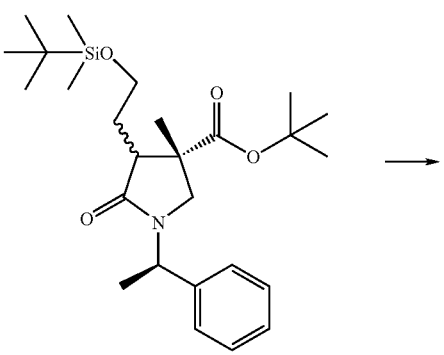

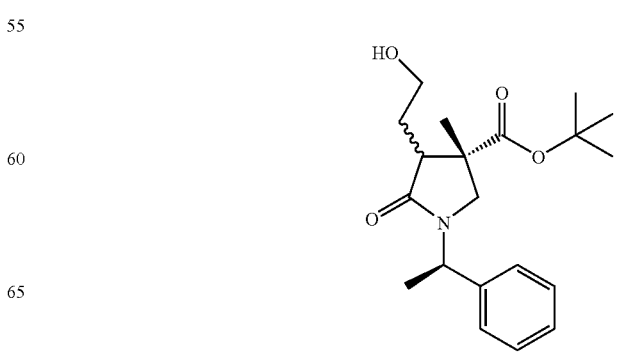

The aforementioned crude silyl compound (54.1 g, 98.9 mmol) was dissolved in tetrahydrofuran (450 mL). A 1.0-mol/L solution of tetrabutylammonium fluoride (148 mmol) in tetrahydrofuran solution mL) was added dropwise to the solution under ice-cooling, and the mixture was stirred at room temperature for 2 hours. The reaction mixture was concentrated, followed by extraction with ethyl acetate (200 mL, 100 mL). The thus-obtained organic layer was washed sequentially with 10% aqueous sodium hydrogencarbonate (200 mL), aqueous citric acid (300 mL), and saturated brine (100 mL), followed by drying over sodium sulfate anhydrate and filtration. The filtrate was evaporated to dryness under reduced pressure. The residue was purified through silica gel column chromatography (eluent; hexane:ethyl acetate=6:1 to 4:1 to 1:1), to thereby yield the title compound as colorless transparent syrup (29.1 g, 83.9 mmol, 85%).

$^1$H-NMR (400 MHz, CDCl$_3$) δ ppm: 1.28 (3H, s) 1.40 (9H, s), 1.51-1.53 (1H, m), 1.53 (3H, d, J=7.1 Hz), 1.78-1.94 (2H, m), 2.90-3.08 (2H, m), 3.67-3.75 (1H, m), 3.80-3.91 (1H, m), 4.85-4.89 (1H, m), 5.43-5.53 (1H, m), 7.27-7.37 (5H, m).

MS (ESI) m/z: 348 (M+H)+.

Referential Example 5 t-Butyl (3S)-4-[2-(benzenesulfonyl)oxyethyl]-3-methyl-5-oxo-1-[(1R)-phenylethyl]pyrrolidine-3-carboxylate

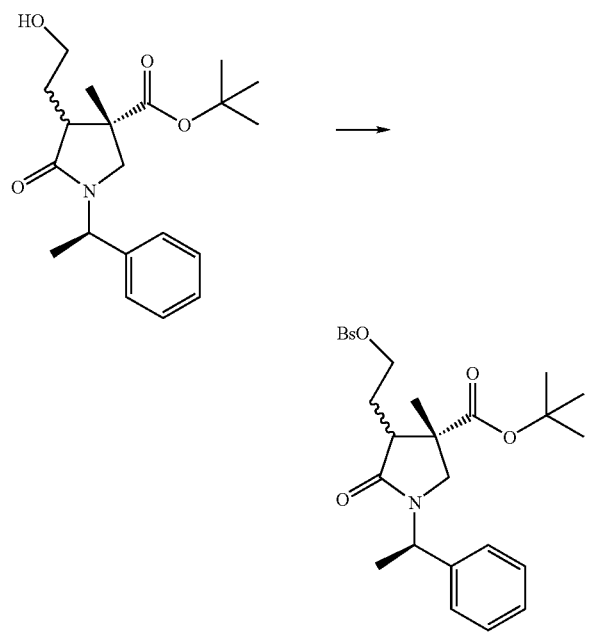

Triethylamine (15.2 mL, 109 mmol), benzenesulfonyl chloride (11.8 mL, 92.3 mmol), and 4-dimethylaminopyridine (1.02 g, 8.39 mmol) were added to a solution of t-butyl (3S)-4-(2-hydroxyethyl)-3-methyl-5-oxo-1-[(1R)-phenylethyl]pyrrolidine-3-carboxylate (29.1 g, 83.9 mmol) in dichloromethane (280 mL) under ice-cooling, and the mixture was stirred at room temperature for 19 hours. Subsequently, saturated aqueous ammonium chloride (280 mL) was added to the reaction mixture. The organic layer was separated, and the solvent thereof was evaporated under reduced pressure. The residue was dissolved in ethyl acetate (280 mL, 180 mL), and the solution was washed again with the same saturated aqueous ammonium chloride as employed above. The formed organic layer was washed sequentially with 1-mol/L aqueous hydrochloric acid (250 mL), saturated aqueous sodium bicarbonate (250 mL), and saturated brine mL), followed by drying over sodium sulfate anhydrate and filtration. The filtrate was evaporated to dryness under reduced pressure, to thereby yield a crude product of the title benzenesulfonyl compound (43.7 g). The thus-obtained compound was used in the subsequent step without performing purification.

MS (ESI) m/z: 510 (M+Na)+.

Referential Example 6 t-Butyl (7S)-7-methyl-4-oxo-5-[(1R)-phenylethyl]-5-azaspiro[2.4]heptane-7-carboxylate

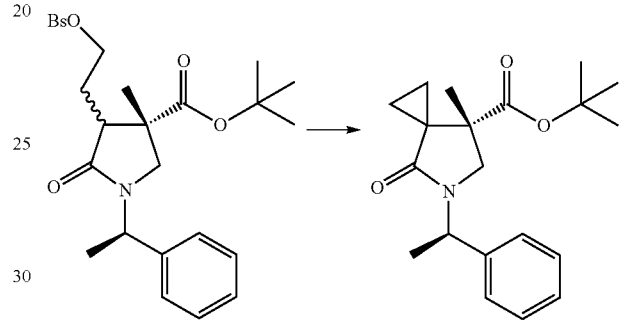

A 1.0-mol/L solution of sodium bis(trimethylsilyl)amide in tetrahydrofuran (109 mL, 109 mmol) was added under ice-cooling to a solution of the crude benzenesulfonyl compound (43.7 g, 83.9 mmol), which had been produced in the previous step, in anhydrous tetrahydrofuran (470 mL). The mixture was stirred at room temperature for 1 hour. Subsequently, saturated aqueous ammonium chloride (300 mL) was added to the reaction mixture, followed by extraction with ethyl acetate (300 mL, 200 mL). The organic layer was washed with saturated brine (200 mL). The formed organic layer was dried over sodium sulfate anhydrate, followed by filtration. The filtrate was evaporated to dryness under reduced pressure. The residue was purified through silica gel column chromatography (eluent; hexane:ethyl acetate=3:1 to 2:1), to thereby yield the title compound as white solid (24.6 g, 89%, 2 steps).

mp: 55-57° C.

[α]$_D$25.1=122.1° (c=0.517, CHCl$_3$).

$^1$H-NMR (400 MHz, CDCl$_3$) δ: 0.72-0.77 (1H, m), 0.85-0.90 (1H, m), 1.04-1.13 (2H, m), 1.18 (3H, s), 1.32 (9H, s), 1.54 (3H, d, J=7.1 Hz), 3.08 (1H, d, J=9.8 Hz), 3.53 (1H, d, J=9.8 Hz), 5.52 (1H, q, J=7.1 Hz), 7.26-7.34 (5H, m).

Elemental Analysis; as $C_{20}H_{27}NO_3$:
Calculated: C, 72.92; H, 8.26; N, 4.25.
Found: C, 72.64; H, 8.27; N, 4.06.
MS (FAB) m/z: 330 (M+H)+.
HRMS (FAB) m/z: 330.2069 (Calcd for C20H28NO3 330.2069).
IR (ATR) ν: 3066, 2976, 2933, 2879, 1720, 1676, 1481, 1454, 1433, 1365, 1329, 1286, 1238, 1203 cm$^{-1}$.

Configuration of the 7-position of the compound was determined through X-ray structural analysis. FIG. 1 shows the detail structure.

After collection of the data, initial phase was determined through the direct method and refined by the complete matrix least square method. In the refining, an anisotropic thermal factor was applied to non-hydrogen atoms, and the positions of hydrogen atoms were fixed in the coordinates through calculation. The compound of Referential Example 6 contains two asymmetric carbon atoms, and absolute configuration of one asymmetric carbon atom is already known. According to this absolute configuration, absolute configuration of the other asymmetric carbon atom was determined.

FIG. 1 shows the results. As shown in FIG. 1, the configuration of the 7-position of the title compound was determined as (S). Thus, configuration of a series of compounds prepared from the compound could also be determined.

Referential Example 7

(7S)-7-Methyl-4-oxo-5-[(1R)-phenylethyl]-5-azaspiro[2.4]heptane-7-carboxylic acid

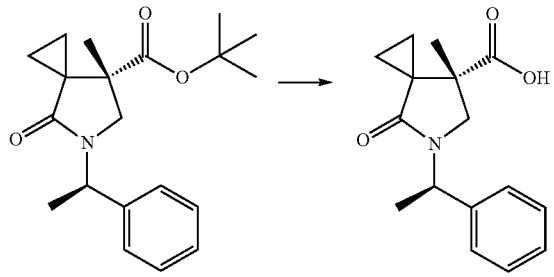

Trifluoroacetic acid (120 mL) was added dropwise to a solution of t-butyl (7S)-7-methyl-4-oxo-5-[(1R)-phenylethyl]-5-azaspiro[2.4]heptane-7-carboxylate (24.5 g, 74.4 mmol) in dichloromethane (120 mL) under ice-cooling, followed by stirring for 2 hours. The reaction mixture was evaporated to dryness under reduced pressure. Toluene (20 mL) was added to the residue, and the mixture was evaporated to dryness under reduced pressure. The residue was dissolved in 1-mol/L aqueous sodium hydroxide (300 mL) under ice-cooling. The resultant aqueous solution was washed with ethyl acetate (350 mL). Concentrated hydrochloric acid (25 mL) was added under ice-cooling to the formed aqueous layer so as to adjust the pH of the layer to 2 to 3, followed by extraction with chloroform (300 mL×2). The formed organic layer was washed sequentially with water (200 mL) and saturated brine (100 mL). The washed layer was dried over sodium sulfate anhydrate, and the solvent was evaporated under reduced pressure. Toluene (20 mL) was added to the residue, and the mixture was evaporated to dryness under reduced pressure. The residue was suspended in chloroform (20 mL), and hexane (200 mL) was added to the suspension for crystallization. The precipitated solid was washed with hexane (100 mL) and dried under reduced pressure, to thereby yield the title compound as white solid (20.48 g (quantitative)). The thus-obtained compound was used in the subsequent step without performing purification.

$^1$H-NMR (400 MHz, CDCl$_3$) δ ppm: 0.78-0.83 (1H, m) 0.90-0.95 (1H, m), 1.08-1.18 (2H, m), 1.24 (3H, s), 1.55 (3H, d, J=7.3 Hz), 3.11 (1H, d, J=10.0 Hz), 3.55 (1H, d, J=10.0 Hz), 5.52 (1H, q, J=7.1 Hz), 7.28-7.32 (5H, m).

MS (ESI) m/z: 274 (M+H)+.

Referential Example 8

(7S)-7-Amino-7-methyl-4-oxo-5-[(1R)-phenylethyl]-5-azaspiro[2.4]heptane

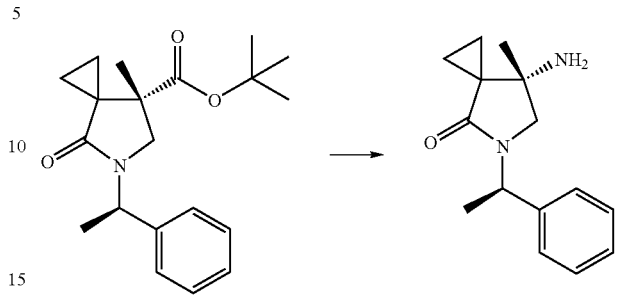

(7S)-7-Methyl-4-oxo-5-[(1R)-phenylethyl]-5-azaspiro[2.4]heptane-7-carboxylic acid (20.4 g, 74.4 mmol) and diphenylphosphoryl azide (17.6 mL, 81.8 mmol) were dissolved in toluene (200 mL), and triethylamine (20.7 mL, 149 mmol) was added to the solution, followed by stirring under heating in an oil bath (at 125° C.) for 1 hour. The reaction mixture was concentrated under reduced pressure, to thereby yield a crude isocyanate compound.

The crude isocyanate compound was dissolved in 1,4-dioxane (180 mL), and water (90 mL) and concentrated hydrochloric acid (90 mL) were added to the solution, followed by stirring under heating in an oil bath (at 50° C.) for 1 hour. Subsequently, water (200 mL) was added to the reaction mixture, and the mixture was washed with ethyl acetate (200 mL). 10-mol/L Aqueous sodium hydroxide (170 mL) was added under ice-cooling to the formed aqueous layer so as to adjust the pH of the layer to 9 to 10, followed by extraction with toluene (200 mL×2). The organic layer was washed with saturated brine (100 mL), dried over sodium sulfate anhydrate, and filtered. The filtrate was concentrated under reduced pressure, to thereby yield the title compound as pale yellow oil (15.8 g, 64.7 mmol). The thus-obtained compound was used in the next step without any purification.

$^1$H-NMR (400 MHz, CDCl$_3$) δ ppm: 0.72-0.78 (2H, m), 0.99-1.10 (2H, m), 1.08 (3H, s), 1.53 (3H, d, J=7.4 Hz), 2.82 (1H, d, J=9.6 Hz), 3.27 (1H, d, J=9.6 Hz), 5.56 (1H, q, J=7.1 Hz), 7.14-7.37 (5H, m).

Referential Example 9

(7S)-7-(t-Butoxycarbonylamino)-7-methyl-5-[(1R)-phenylethyl]-5-azaspiro[2.4]heptane

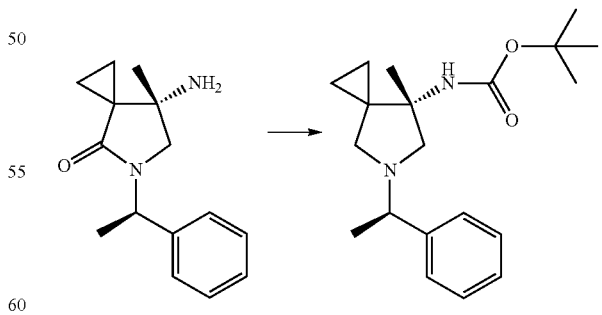

The aforementioned (7S)-7-amino-7-methyl-4-oxo-5-[(1R)-phenylethyl]-5-azaspiro[2.4]heptane (15.8 g, 64.7 mmol) was dissolved in toluene (82 mL). Separately, 65 wt. % sodium bis(2-methoxyethoxy)aluminum hydride (259 mmol) in toluene (77.6 mL) was prepared, and an aliquot (6 mL) of the solution was added dropwise to the azaspiroheptane solution over 15 minutes. Through ice-cooling, the internal temperature of the reaction mixture was controlled so as not to exceed 70° C. The resultant mixture was stirred under heating in an oil bath (at 80° C.) for 10 minutes. The reaction mixture was ice-cooled, and 25 wt. % aqueous sodium hydroxide (158 mL) was added dropwise thereto for termination of reaction, followed by extraction with toluene (135 mL). The formed organic layer was washed with saturated brine (100 mL), and di-t-butyl dicarbonate (15.6 g, 71.2 mmol) was added to the washed layer. The reaction mixture was stirred at room temperature for 3 hours, and the solvent was evaporated under reduced pressure. The residue was purified through silica gel column chromatography (eluent; hexane:ethyl acetate=8:1 to 4:1 to 1:1), to thereby yield the title compound as colorless transparent syrup (18.0 g, 73%).

$^1$H-NMR (400 MHz, CDCl$_3$) δ ppm: 0.37-0.49 (2H, m), 0.62-0.68 (1H, m), 0.77-0.82 (1H, m), 1.20 (3H, s), 1.32 (3H, d, J=6.6 Hz), 1.44 (9H, s), 2.46 (2H, dd, J=33.2, 9.3 Hz), 2.68 (1H, d, J=8.8 Hz), 3.27 (1H, q, J=6.6 Hz), 3.31-3.34 (1H, m), 4.71 (1H, s), 7.19-7.34 (5H, m).

MS (ESI) m/z: 331 (M+H)+.

Referential Example 10

(7S)-7-(t-Butoxycarbonylamino)-7-methyl-5-azaspiro[2.4]heptane

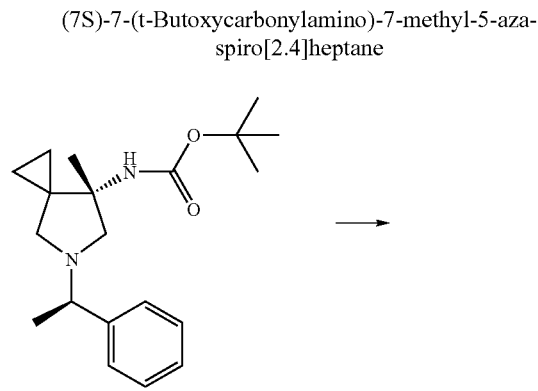

To a solution of (7S)-7-(t-butoxycarbonylamino)-7-methyl-5-[(1R)-phenylethyl]-5-azaspiro[2.4]heptane (18.0 g, 54.5 mmol) in methanol (180 mL), 10% palladium carbon (water content: 52.8%, 9.00 g) serving as a catalyst was added, and the mixture was stirred at room temperature under a hydrogen gas atmosphere for 18 hours. The mixture was further stirred in an oil bath (at 40° C.) for 5.5 hours. The catalyst was removed through filtration, and the solvent was evaporated to dryness under reduced pressure, to thereby yield a crude product of the title compound as white solid (13.4 g (quantitative)).

$^1$H-NMR (400 MHz, CDCl$_3$) δ ppm: 0.38-0.43 (1H, m) 0.54-0.61 (2H, m), 0.74-0.80 (1H, m), 1.08 (3H, s), 1.44 (9H, s), 2.75 (1H, d, J=7.6 Hz), 2.78 (1H, d, J=7.1 Hz), 3.13 (1H, d, J=11.5 Hz), 3.73-3.77 (1H, m), 4.45 (1H, s).

MS (ESI) m/z: 227 (M+H)+.

Referential Example 11

7-[(7S)-7-Amino-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid

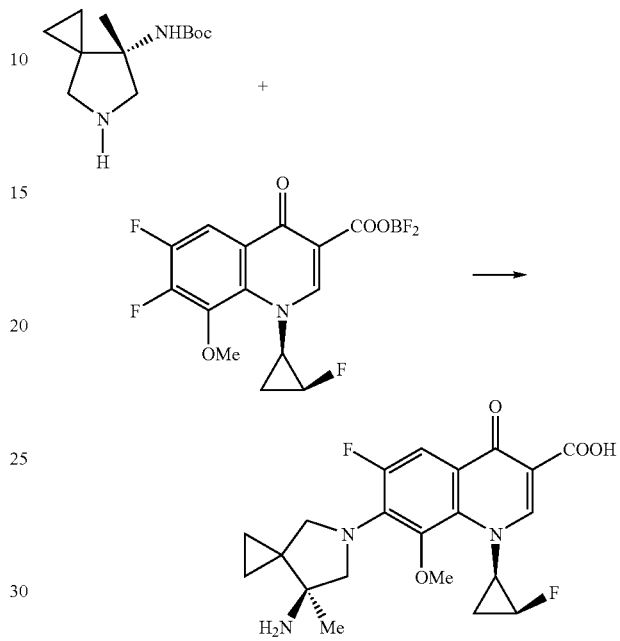

(7S)-7-(t-Butoxycarbonylamino)-7-methyl-5-azaspiro [2.4]heptane (13.4 g, 54.5 mmol), 6,7-difluoro-1-[(1R,2S)-2-fluorocyclopropyl]-8-methoxy-1,4-dihydro-4-oxoquinoline-3-carboxylic acid-difluoroboron complex (17.9 g, 49.5 mmol), and triethylamine (8.97 mL, 64.4 mmol) were dissolved in dimethyl sulfoxide (52 mL), followed by stirring under heating in an oil bath (at 40° C.) for 17 hours. The reaction mixture was poured into cold water (1,000 mL), and the precipitated solid was collected through filtration. Triethylamine (15 mL) and a mixture (180 mL) of ethanol and water (5:1) were added to the solid, followed by refluxing for 1.5 hours. The reaction mixture was evaporated to dryness under reduced pressure. The residue was dissolved in ethyl acetate (150 mL×2), followed by washing sequentially with 10% aqueous citric acid (200 mL), water (200 mL), and saturated brine (100 mL). The organic layer was dried over sodium sulfate anhydrate, and the solvent was evaporated under reduced pressure. The residue was dissolved in a mixture (100 mL) of chloroform and methanol (9:1), and silica gel (10 g) was added to the solution, followed by stirring for 1 hour. Thereafter, silica gel was removed from the mixture through filtration, and the silica gel was washed with a mixture of chloroform and methanol (9:1) (50 mL×2). The filtrate and washings were combined, followed by concentration to dryness. The residue was dissolved in concentrated hydrochloric acid (200 mL) under ice-cooling, and the solution was stirred at room temperature for 30 minutes. The reaction mixture was washed with chloroform (400 mL×5). 10-mol/L Aqueous sodium hydroxide was added under ice-cooling to the formed aqueous layer so as to adjust the pH of the layer to 11.8. Subsequently, the pH of the layer was adjusted to 7.4 with hydrochloric acid, followed by extraction with chloroform (1,000 mL×3). The organic layer was dried over sodium sulfate anhydrate, and the solvent was evaporated under reduced pressure. The residue was recrystallized from ethanol for purification and dried under reduced pressure, to thereby yield the title compound as pale pink powder (18.5 g, 79%).

Analytical data of the resultant product obtained by means of apparatuses including $^1$H-NMR completely coincided with those of the compound of Example 23. Thus, among quinolone derivatives having a 7-amino-7-methyl-5-azaspiro[2.4]heptan-5-yl group, the 7-position configuration of the 5-azaspiro[2.4]heptan-5-yl group of the quinolone derivative described in Example 23, which is a highly active compound, was determined as (7S).

The compounds produced in Examples 12, 13, 14, 16, 17, and 20, and the compound which had been reacted with the boron-chelate compound in Example 21 were (S)-forms. The compounds produced in Examples 15 and 18 and the compound which had been reacted with the boron-chelate compound in Example 22 were (R)-forms.

The invention claimed is:

1. A compound represented by formula (1)

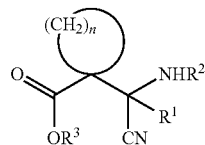

(1)

wherein n is an integer of 2 to 5; $R^1$ represents a C1 to C4 alkyl group which may have a substituent or an aryl group which may have a substituent; $R^2$ represents an alkoxycarbonyl group which may have a substituent, an aralkyloxycarbonyl group which may have a substituent, an aliphatic acyl group which may have a substituent, or an aromatic acyl group which may have a substituent; and $R^3$ represents a C1 to C4 alkyl group which may have a substituent, an aralkyl group which may have a substituent, or a hydrogen atom.

2. The compound as described in claim 1, wherein, in formula (1), n is 2.

3. The compound as described in claim 1, wherein, in formula (1), $R^2$ is a t-butyloxycarbonyl group, a benzyloxycarbonyl group, a benzoyl group, or an acetyl group.

4. The compound as described in any one of claim 1, wherein, in formula (1), $R^1$ is a methyl group, an ethyl group, a propyl group, an isopropyl group, or a phenyl group.

5. The compound as described in any one of claim 1, wherein, in formula (1), $R^3$ is a methyl group or an ethyl group.

* * * * *